US011311257B2

(12) United States Patent
Martinez Ferreira et al.

(10) Patent No.: US 11,311,257 B2
(45) Date of Patent: Apr. 26, 2022

(54) SYSTEMS AND METHODS FOR A MOBILE X-RAY IMAGING SYSTEM

(71) Applicant: General Electric Company, Schenectady, NY (US)

(72) Inventors: Carlos Martinez Ferreira, Paris (FR); Jean-Michel Marteau, Le Plessis Robinson (FR); Julien Marcotte, Saint-Vrain (FR); Herve Buffard, Mirabeau (FR); Sebastien Roquand, Guyancourt (FR)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 16/529,663

(22) Filed: Aug. 1, 2019

(65) Prior Publication Data
US 2020/0054297 A1 Feb. 20, 2020

Related U.S. Application Data

(60) Provisional application No. 62/718,807, filed on Aug. 14, 2018.

(51) Int. Cl.
*A61B 6/00* (2006.01)
*A61B 6/03* (2006.01)

(52) U.S. Cl.
CPC ............ *A61B 6/4405* (2013.01); *A61B 6/032* (2013.01); *A61B 6/4441* (2013.01); *A61B 6/4458* (2013.01); *A61B 6/4447* (2013.01); *A61B 6/588* (2013.01)

(58) Field of Classification Search
CPC ... A61B 6/4405; A61B 6/4441; A61B 6/4447; A61B 6/4458; A61B 6/588; A61B 6/447; A61B 6/032
See application file for complete search history.

(56) References Cited

U.S. PATENT DOCUMENTS

| | | | | | |
|---|---|---|---|---|---|
| 5,479,470 | A | * | 12/1995 | Stenfors | A61B 6/4441 378/197 |
| 6,869,217 | B2 | * | 3/2005 | Rasche | A61B 6/4464 378/197 |
| 7,261,464 | B2 | * | 8/2007 | Noda | A61B 6/4441 378/197 |
| 7,597,473 | B2 | | 10/2009 | Rainer | |

(Continued)

FOREIGN PATENT DOCUMENTS

| CN | 105011957 | * 11/2015 |
|---|---|---|
| CN | 105011957 A | * 11/2015 |

(Continued)

OTHER PUBLICATIONS

English translation of CN105011957A (Year: 2015).*

(Continued)

*Primary Examiner* — Dani Fox
*Assistant Examiner* — Soorena Kefayati

(57) ABSTRACT

Various methods and systems are provided for a mobile x-ray imaging system. In one embodiment, a system includes a gantry with an x-ray source and an x-ray detector mounted thereon opposite each other, a carrier coupled to the gantry and configured to rotate the gantry relative to the carrier, and a robotic arm coupling the carrier to a base, the robotic arm comprising at least three links and four joints.

12 Claims, 18 Drawing Sheets

(56) References Cited

U.S. PATENT DOCUMENTS

| | | | |
|---|---|---|---|
| 7,748,900 B2* | 7/2010 | Maschke | A61B 6/4458 378/197 |
| 7,905,658 B2 | 3/2011 | Gro et al. | |
| 8,534,916 B2* | 9/2013 | Maschke | A61B 6/4458 378/197 |
| 8,708,561 B2* | 4/2014 | Eaves | A61B 6/4405 378/198 |
| 8,961,010 B2* | 2/2015 | Meyer | A61B 6/4441 378/197 |
| 9,033,575 B2* | 5/2015 | Martinez Ferreira | A61B 6/587 378/197 |
| 9,439,605 B2* | 9/2016 | Schäfer | A61B 6/4441 |
| 10,751,011 B2* | 8/2020 | Hou | A61B 6/4464 |
| 2002/0118793 A1* | 8/2002 | Horbaschek | A61B 6/4233 378/197 |
| 2003/0001056 A1* | 1/2003 | Ihalainen | F16M 11/2092 248/276.1 |
| 2003/0147504 A1* | 8/2003 | Hanover | A61B 6/4441 378/197 |
| 2004/0202284 A1* | 10/2004 | Graumann | A61B 6/4441 378/195 |
| 2005/0251010 A1* | 11/2005 | Mistretta | A61B 6/481 600/407 |
| 2006/0078091 A1* | 4/2006 | Lasiuk | G01N 23/04 378/198 |
| 2006/0153340 A1* | 7/2006 | Engstrom | A61B 6/4441 378/197 |
| 2007/0003014 A1* | 1/2007 | Boese | A61B 6/4476 378/95 |
| 2007/0211863 A1* | 9/2007 | Graumann | A61B 6/4441 378/197 |
| 2007/0268994 A1* | 11/2007 | Chen | A61B 6/027 378/4 |
| 2008/0075225 A1* | 3/2008 | Kalender | A61B 6/4458 378/20 |
| 2008/0101546 A1* | 5/2008 | Delmas | A61B 6/4464 378/197 |
| 2009/0024025 A1* | 1/2009 | Maschke | A61B 6/505 606/86 R |
| 2009/0097612 A1* | 4/2009 | Rauch | A61B 6/03 378/19 |
| 2009/0180592 A1* | 7/2009 | Gross | A61B 6/4458 378/197 |
| 2009/0271035 A1* | 10/2009 | Lurz | B25J 9/1664 700/245 |
| 2010/0114308 A1* | 5/2010 | Maschke | A61B 6/12 623/2.37 |
| 2011/0066022 A1* | 3/2011 | Fadler | A61B 6/56 600/407 |
| 2011/0280379 A1* | 11/2011 | Maschke | A61B 6/4458 901/15 |
| 2012/0262154 A1* | 10/2012 | Gro | A61B 6/4441 73/488 |
| 2012/0314843 A1* | 12/2012 | Limmer | A61B 6/4441 378/197 |
| 2013/0003939 A1* | 1/2013 | Bouvier | A61B 6/548 378/198 |
| 2013/0243166 A1* | 9/2013 | Moulin | H05G 1/02 378/197 |
| 2014/0086393 A1* | 3/2014 | Graumann | A61B 6/4464 378/198 |
| 2015/0139396 A1* | 5/2015 | Klingenbeck | A61B 6/4014 378/62 |
| 2015/0335387 A1* | 11/2015 | Atzinger | F16H 13/16 606/130 |
| 2015/0342546 A1* | 12/2015 | Zaiki | A61B 6/503 378/62 |
| 2016/0015345 A1* | 1/2016 | Noda | A61B 6/504 378/197 |
| 2016/0082596 A1* | 3/2016 | Barth | B25J 5/00 901/1 |
| 2016/0089093 A1* | 3/2016 | Mao | A61B 6/4441 378/198 |
| 2016/0135775 A1* | 5/2016 | Mistretta | G06T 7/0012 600/419 |
| 2017/0020468 A1* | 1/2017 | Bouvier | A61B 6/4405 |
| 2017/0084027 A1* | 3/2017 | Mintz | A61B 1/0016 |
| 2019/0053774 A1* | 2/2019 | Weingarten | B25J 9/1666 |

FOREIGN PATENT DOCUMENTS

| | | |
|---|---|---|
| CN | 105011957 A | 11/2015 |
| CN | 108056783 A | 5/2018 |
| JP | 2008516238 A | 5/2008 |
| WO | 2011067648 A1 | 6/2011 |

OTHER PUBLICATIONS

English translation of CN 105011957 (Year: 2015).*
European application 19191355.7 filed Aug. 12, 2019; Search Report dated Dec. 18, 2019, 6 pages.
JP application 2019-147389 filed Aug. 9, 2019—Office Action dated Dec. 7, 2021—Machine Translation Dec. 8, 2021; 6 pages.

* cited by examiner

SYSTEMS AND METHODS FOR A MOBILE X-RAY IMAGING SYSTEM

CROSS REFERENCE TO RELATED APPLICATIONS

The present application claims priority to U.S. Provisional Patent Application No. 62/718,807, entitled "SYSTEMS AND METHODS FOR A MOBILE X-RAY IMAGING SYSTEM", filed on Aug. 14, 2018. The entire contents of the above-listed application are incorporated herein by reference for all purposes.

FIELD

Embodiments of the subject matter disclosed herein relate to x-ray imaging systems, and particularly to mobile x-ray imaging system gantries.

BACKGROUND

It is frequently desired to conduct an x-ray examination of a patient from several different positions and is often preferable to do so without the need to reposition the patient. Mobile C-arm x-ray imaging systems have been developed to meet these needs and are now well-known in the medical and surgical arts. The C-arm x-ray imaging system is especially useful in that it is small enough and mobile enough to be present in an operating or exam situation without requiring the physician to repeatedly move or requiring the patient to change positions to obtain a suitable image.

The term "C-arm" refers to the generally C-shaped gantry of the machine, to which an x-ray source and an x-ray detector are mounted on opposing ends of the C-arm such that x-rays emitted by the x-ray source are incident on and detected by the x-ray detector. The x-ray source and x-ray detector are positioned such that when, for example, a human extremity is interposed between the x-ray source and the x-ray detector and irradiated with x-rays, the x-ray detector produces data representative of characteristics of the interposed object. The data produced is typically displayed on a monitor and electronically stored.

BRIEF DESCRIPTION

In one embodiment, a system comprises a gantry with an x-ray source and an x-ray detector mounted thereon opposite each other, a carrier coupled to the gantry and configured to rotate the gantry relative to the carrier, and a robotic arm coupling the carrier to a mobile base and configured to adjust a position of the carrier relative to the mobile base, wherein the robotic arm comprises three links and four joints. In this way, a mobile x-ray imaging system may have an increased isocenter displacement and range of motion.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
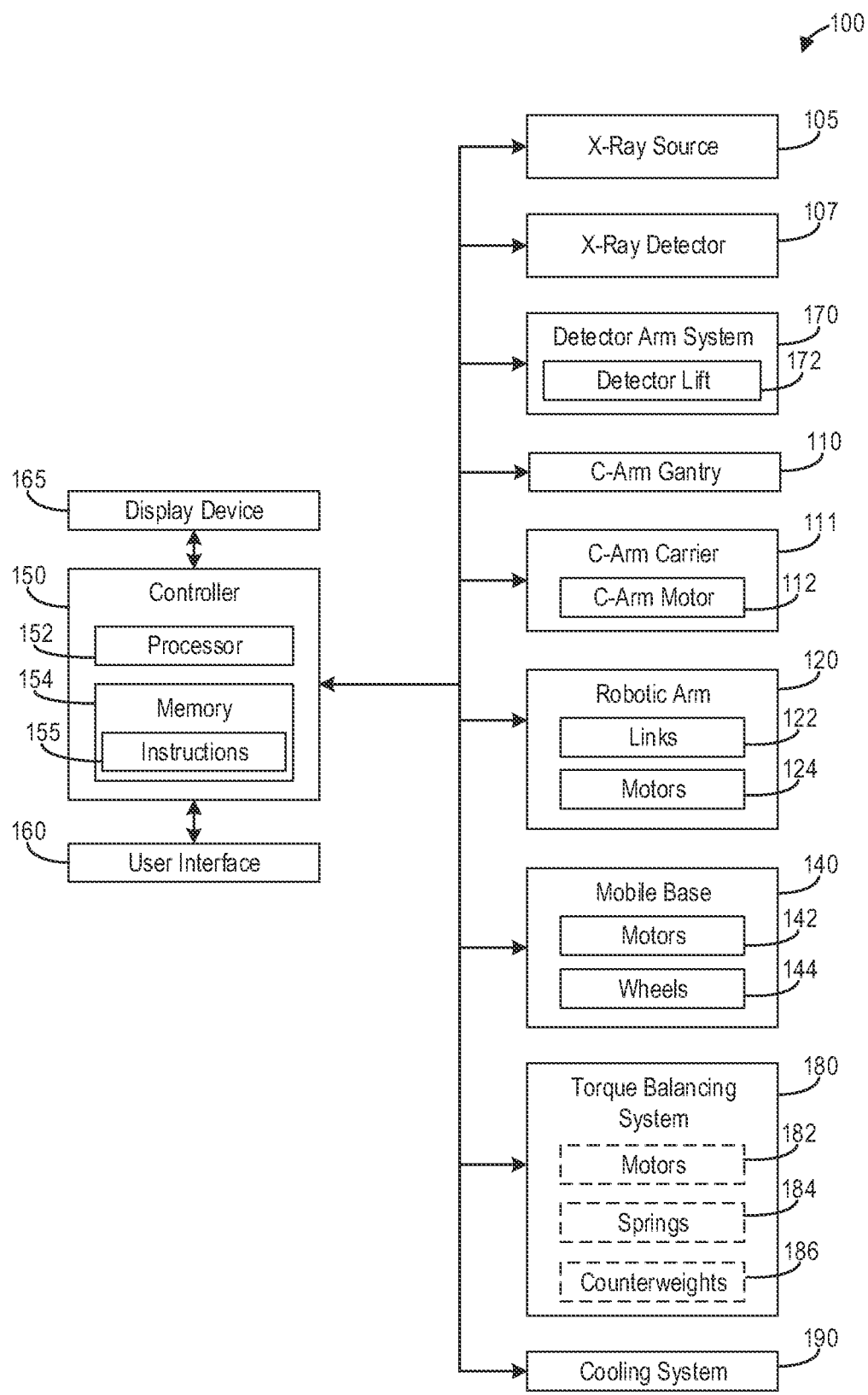
FIG. 1 shows a block diagram illustrating components of an example mobile x-ray imaging system according to an embodiment.
Figure 2:
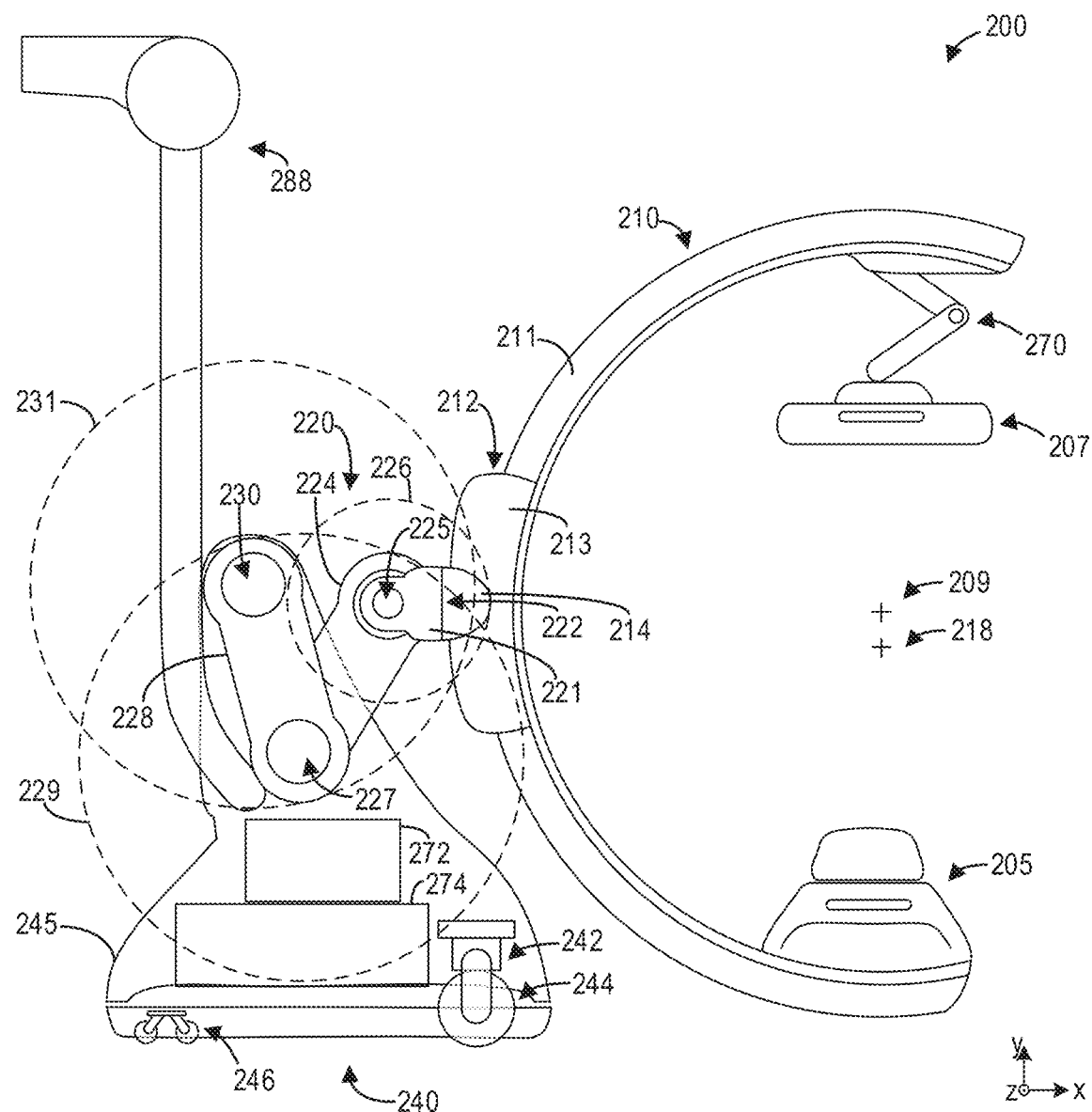
FIG. 2 shows a schematic illustration of an example mobile x-ray imaging system in a first articulated configuration according to an embodiment.
Figure 3:
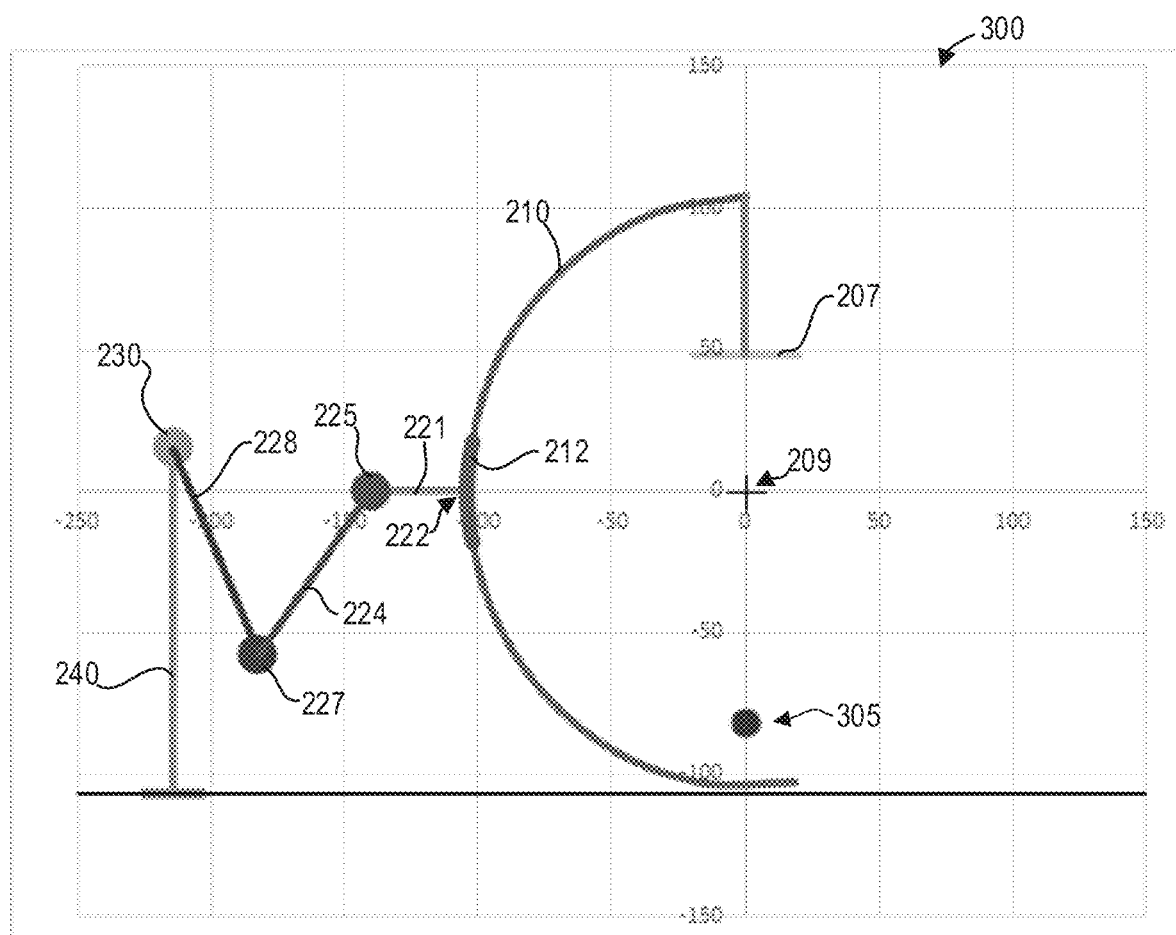
FIG. 3 shows a simplified diagram illustrating the example mobile x-ray imaging system in the first articulated configuration according to an embodiment.
Figure 10:
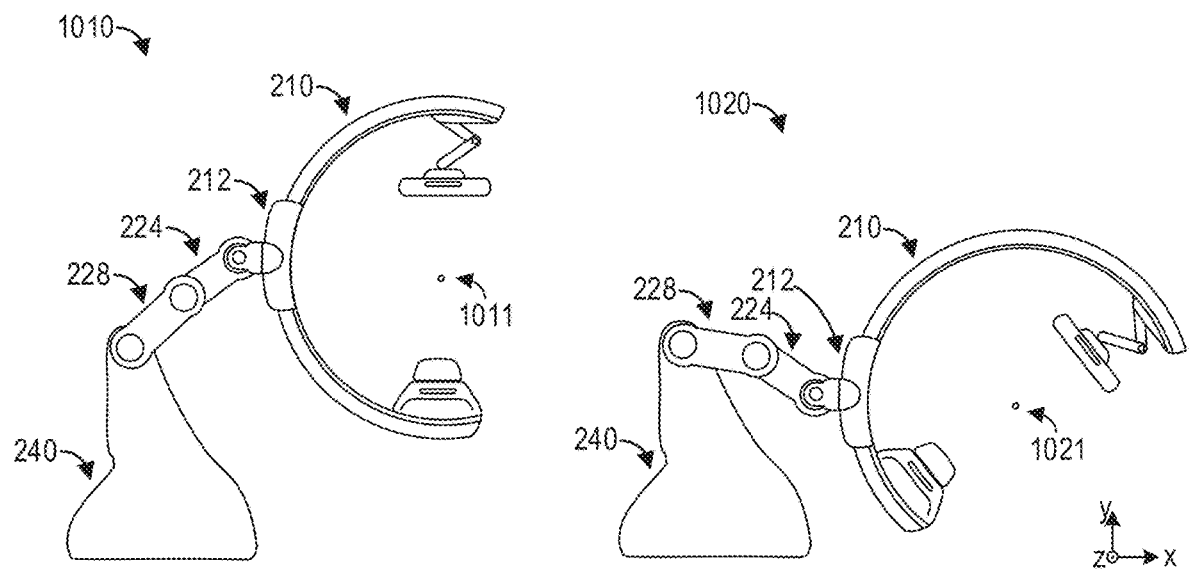
FIG. 10 shows a schematic illustration depicting the example mobile x-ray imaging system moving from a first to a second articulated configuration.
Figure 11:
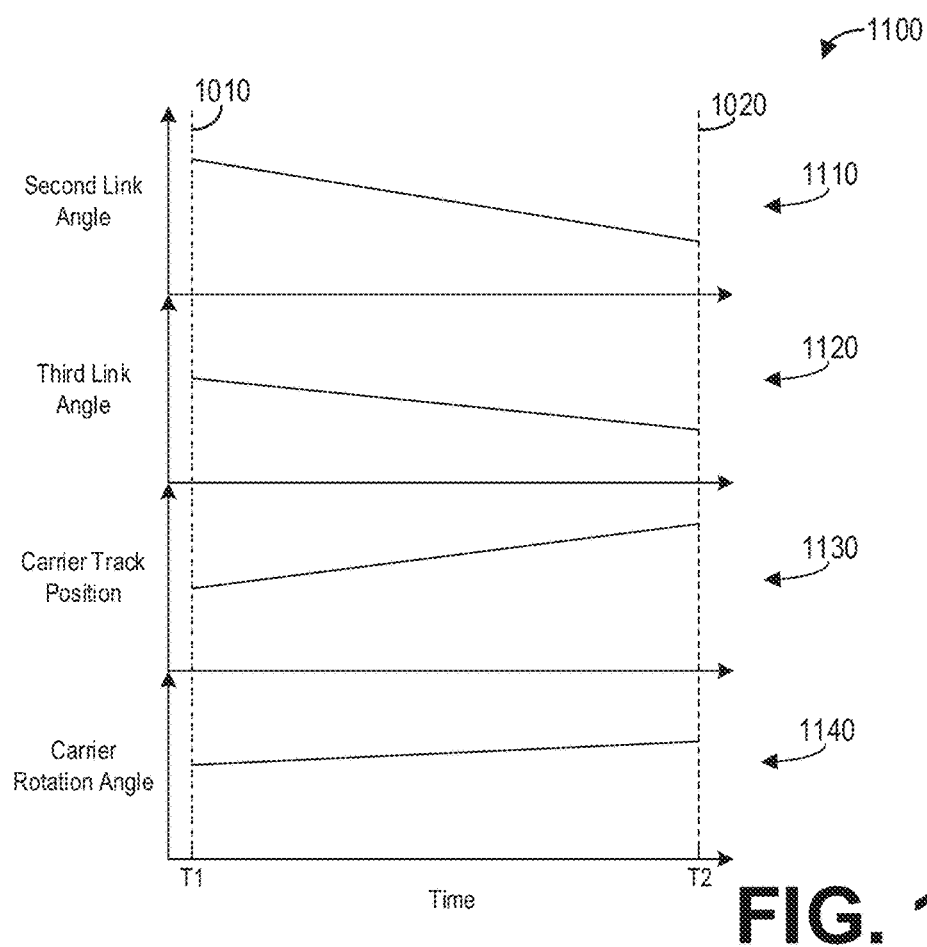
FIGS. 11-13 depict different example trajectories for adjusting components of the mobile x-ray imaging system from the first to the second articulated configuration.
Figure 12:
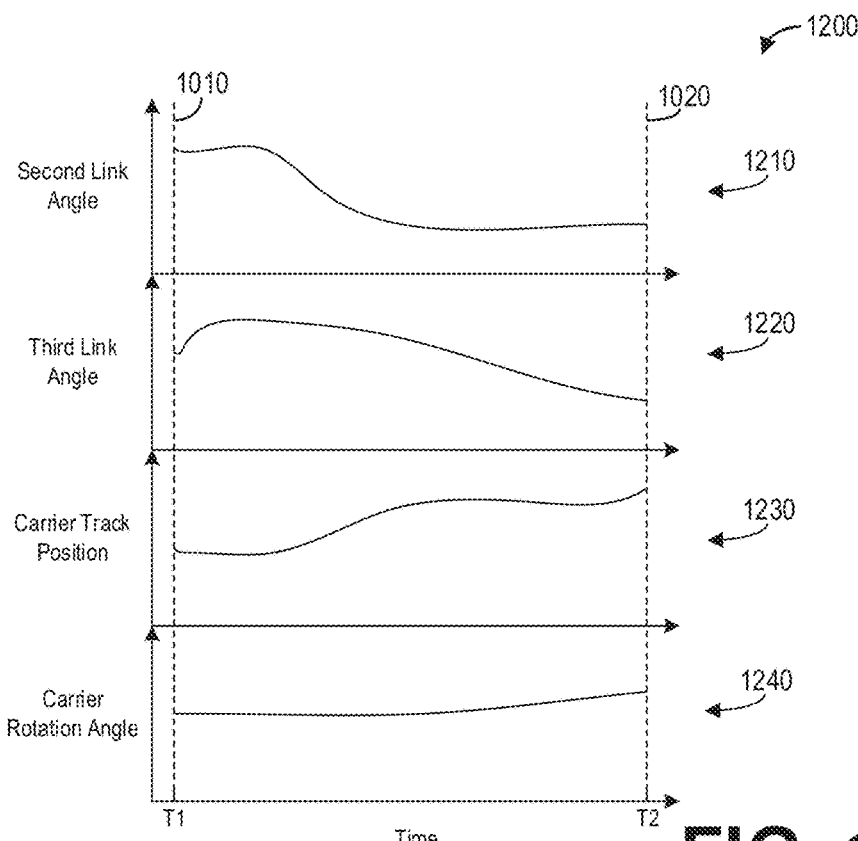
Figure 13:
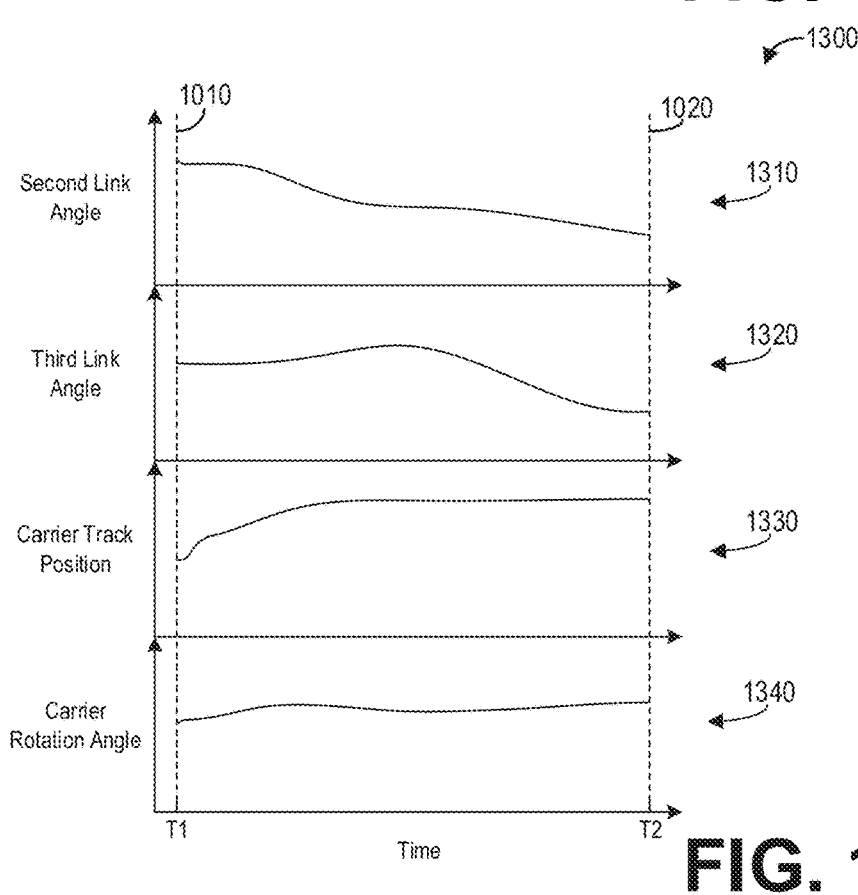
Figure 16:
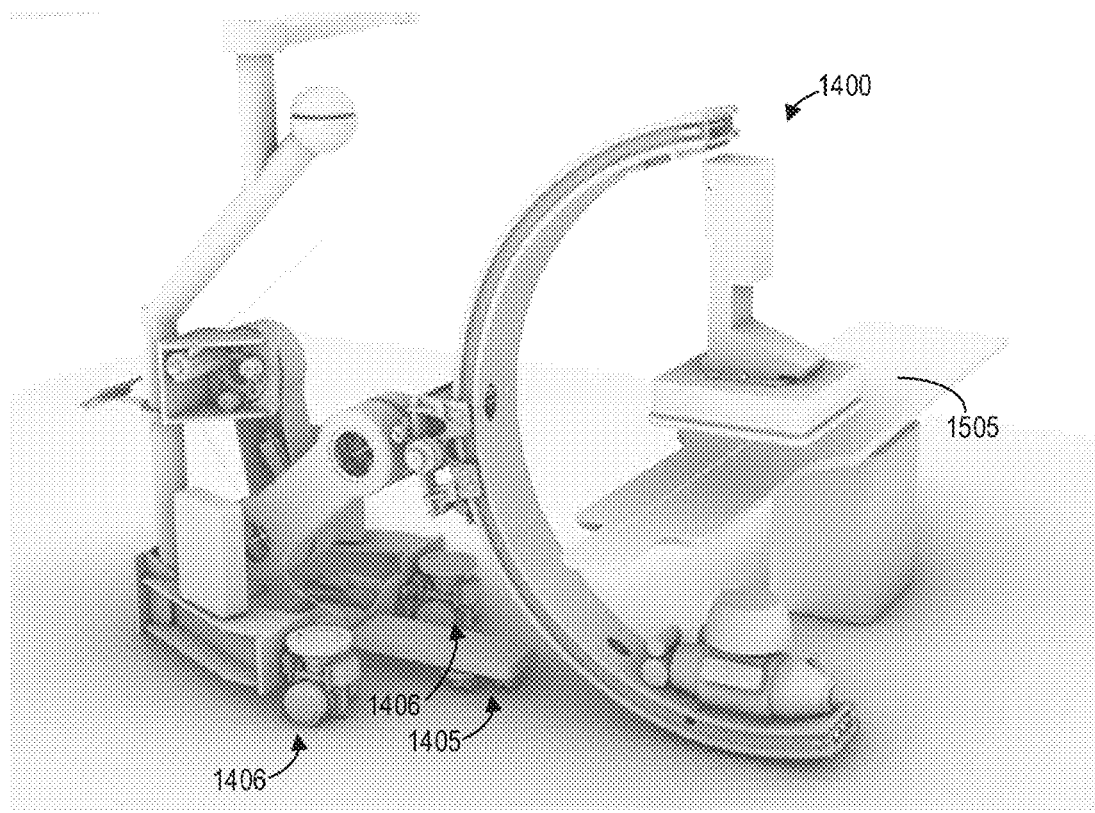
FIGS. 16 and 17 show perspective pictorial views of the example mobile x-ray imaging system of FIG. 14.
Figure 17:
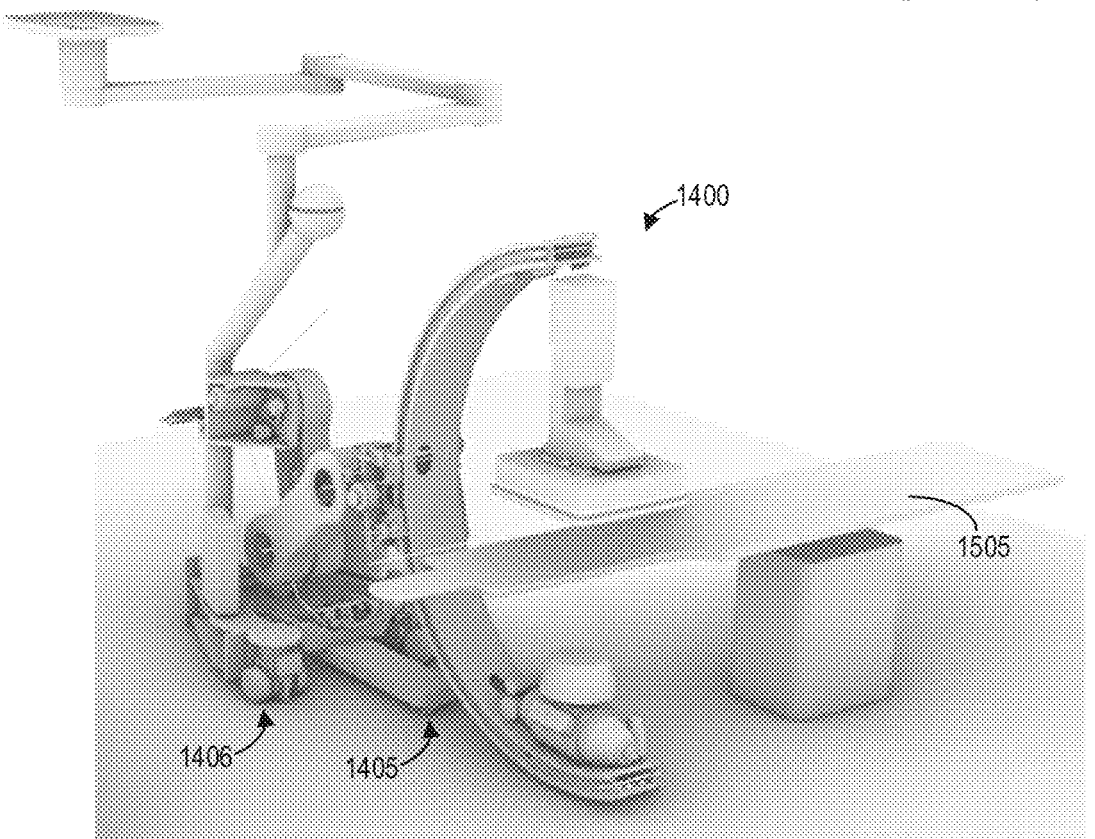
Figure 18:
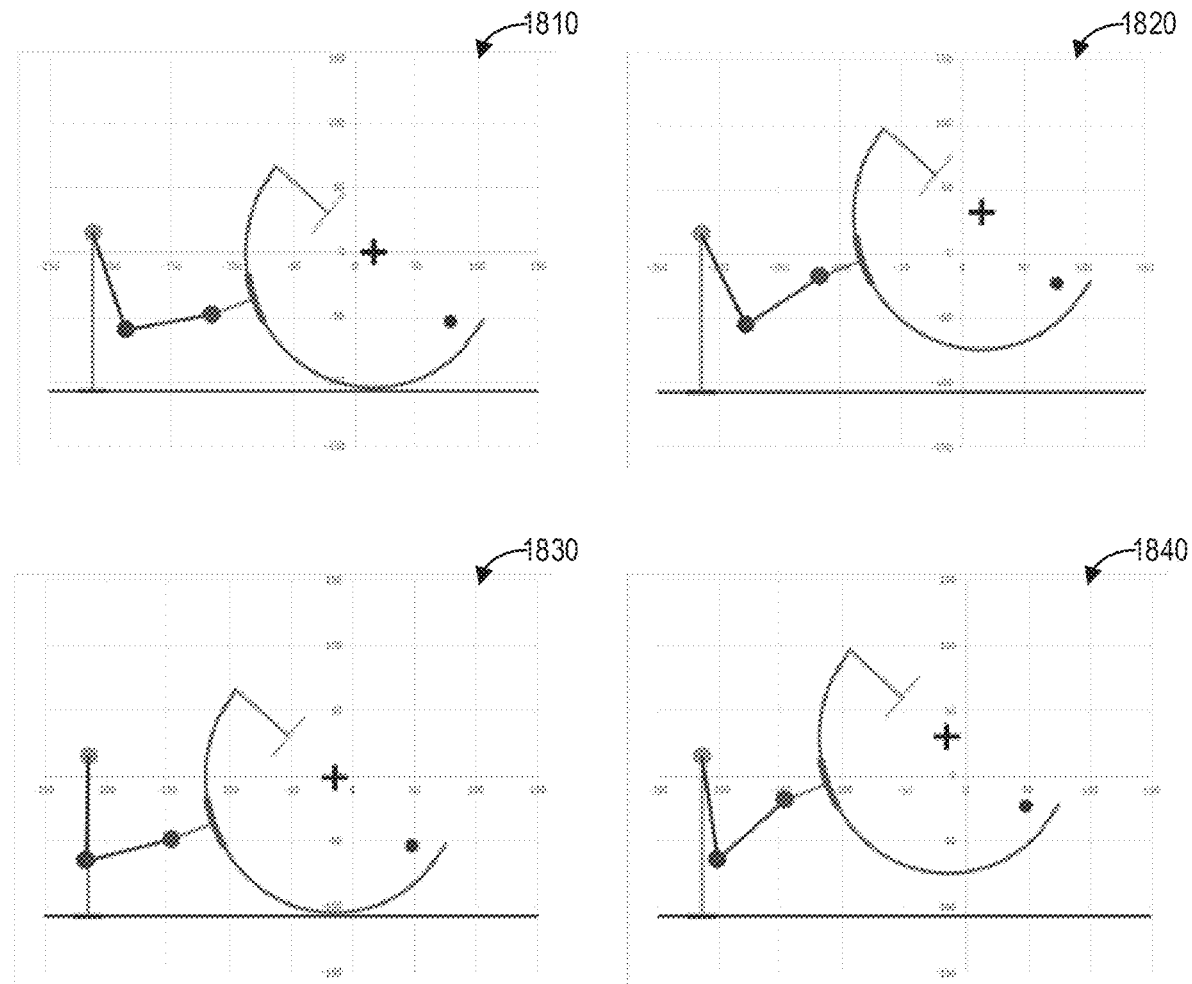
FIG. 18 shows a set of simplified diagrams illustrating example articulated configurations for adjusting the isocenter position.
Figure 19:
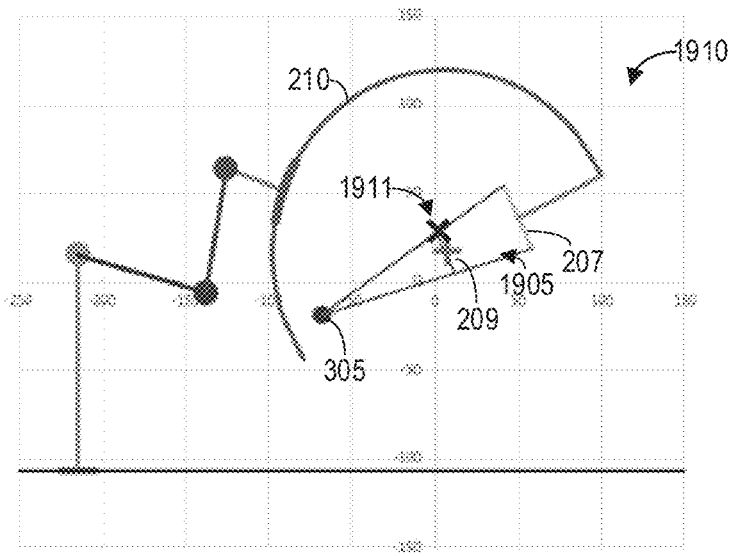
FIG. 19 shows a set of simplified diagrams illustrating dynamic rotations around a point different from the isocenter according to an embodiment.
Figure 19:
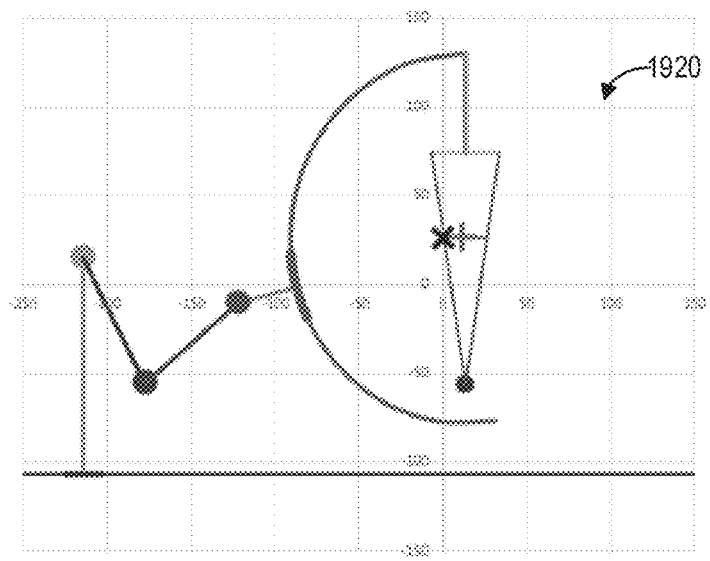
Figure 19:
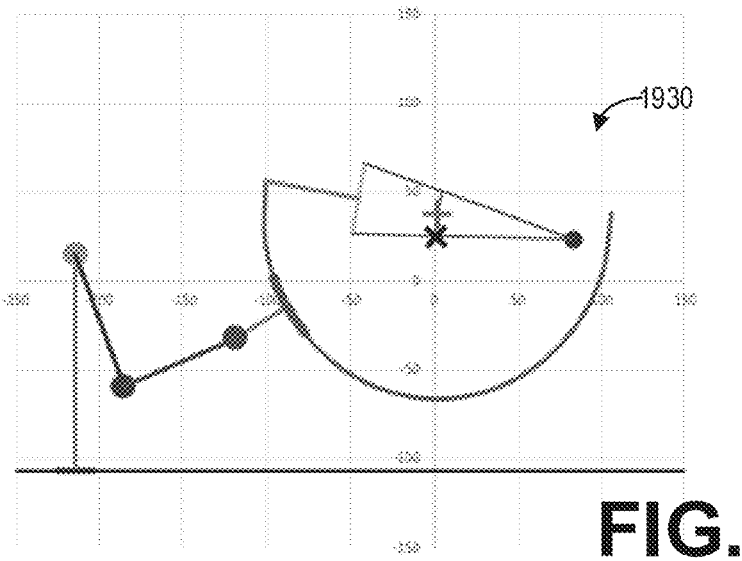

The following description relates to various embodiments of a mobile x-ray imaging system. As depicted in FIGS. 1-3, a mobile x-ray imaging system may include a robotic arm with at least three links and four joints for adjusting a position of a C-arm carrier, and thus a C-arm gantry coupled thereto, relative to a mobile base. The configuration of the links of the robotic arm enables an increased range of motion for achieving a desired isocenter position, as depicted in FIGS. 4-7. The mobile x-ray imaging system may include a torque balancing system, such as a spring-based torque balancing system as depicted in FIG. 8, for reducing the load on the motors of the robotic arm. A method for controlling a mobile x-ray imaging system, such as the method depicted in FIG. 9, includes determining position adjustments to one or more components of the mobile x-ray imaging system to align an isocenter of the imaging system with a desired isocenter position. To adjust the isocenter of the mobile x-ray imaging system from a first position to a second position, as depicted in FIG. 10, multiple different trajectories may be used, as depicted in FIGS. 11-13, according to various considerations such as weight balancing, obstacles within the room, the length of the links of the robotic arm, and so on. An example mobile x-ray imaging system with a different wheel configuration is depicted in FIGS. 14-17. FIG. 18 depicts example articulated configurations of the robotic arm to adjust the isocenter position. FIG. 19, meanwhile, depicts example articulated configurations for rotating the C-arm gantry around a point other than isocenter. Dynamically rotating the x-ray source and x-ray detector during imaging around a point other than isocenter allows for different isocenter trajectories, and thus a variety of x-ray imaging modes, as depicted in FIGS. 20-26.

FIG. 1 shows a block diagram illustrating components of an example mobile x-ray imaging system 100. The mobile x-ray imaging system 100 comprises an x-ray source 105 and an x-ray detector 107 mounted on a C-arm gantry 110.

The detector arm system 170 includes a detector arm motor or detector lift 172 for adjusting the position of the x-ray detector 107. For example, as discussed further herein, the detector lift 172 may translate and/or rotate the x-ray detector 107 relative to the C-arm gantry 110.

The C-arm gantry 110 includes a C-arm motor 112 for adjusting the position of the C-arm gantry 110. More specifically, the C-arm gantry 110 is mechanically coupled to a C-arm carrier 111 which includes the C-arm motor 112, and the C-arm motor 112 may be driven to adjust the position of the C-arm gantry 110 with respect to the C-arm carrier 111, as described further herein with regard to FIGS. 2-5.

The mobile x-ray imaging system 100 further comprises a robotic arm 120 mechanically coupled to the C-arm gantry 110 via the C-arm carrier 111. The robotic arm 120 includes a plurality of links 122 and motors 124 positioned at joints between the links 122, as described further herein. In particular, the plurality of links 122 of the robotic arm 120 includes a first link coupled to the C-arm carrier 111 and thus forming a first motorized joint between the first link and the C-arm carrier 111 for adjusting a position of the C-arm carrier 111 relative to the first link, a second link coupled to the first link and thus forming a second motorized joint between the first link and the second link for adjusting a position of the first link relative to the second link, and a third link coupled to the second link and thus forming a third motorized joint between the second link and the third link for adjusting a position of the second link relative to the third link. Furthermore, the third link is mechanically coupled to the mobile base 140, thus forming a fourth motorized joint between the third link and the mobile base 140 for adjusting a position of the third link relative to the mobile base 140.

The mobile base 140 includes one or more motors 142 for driving one or more wheels 144 to adjust a position of the mobile base 140. In addition, one or more of the wheels 144 may be free or un-motorized, as described further herein. For example, the wheels 144 may comprise two motorized wheels (with two motors 142 per motorized wheel) and one non-motorized wheel.

The mobile x-ray imaging system 100 further includes a controller 150 comprising a processor 152 and a non-transitory memory 154. A method for controlling the mobile x-ray imaging system 100 may be stored as executable instructions 155 in the non-transitory memory 154 and executed by the processor 152. An example method that may be implemented as the instructions 155 is described further herein with regard to FIG. 6.

The mobile x-ray imaging system 100 further include a user interface 160 for receiving input from a user or operator of the mobile x-ray imaging system 100. The user interface 160 may be communicatively coupled to the controller 150 for providing commands input by a user via the user interface 160 to the controller 150. The user interface 160 may comprise one or more of a keyboard, a mouse, a trackball, one or more knobs, one or more joysticks, a touchpad, a touchscreen, one or more hard and/or soft buttons, a smartphone, a microphone, a virtual reality apparatus, and so on. The user interface 160 may thus enable voice control, and display of information such as simulated motion or possible collisions using the virtual reality apparatus or an interactive display device (e.g., touchscreen). In some examples the user interface 160 may be remotely located relative to the mobile x-ray imaging system 100. For example, the user interface 160 may be communicatively coupled to the controller 150 and/or the mobile x-ray imaging system 100 via a wired or wireless connection, and may be positioned away from the mobile base 140.

As discussed further herein, a user of the mobile x-ray imaging system 100 may input a desired isocenter position via the user interface 160, for example. The controller 150 may then determine position adjustments to one or more of the detector arm system 170, the C-arm gantry 110, the robotic arm 120, and the mobile base 140 to align an isocenter of the mobile x-ray imaging system 100 with the desired isocenter position. As another example, a user of the mobile x-ray imaging system 100 may directly control the position of one or more components of the mobile x-ray imaging system 100 relative to other components of the mobile x-ray imaging system 100 via the user interface 160. For example, the user may directly input, via a joystick or knob, for example, position adjustments to one or more components of the mobile x-ray imaging system 100. As another example, the motion of the components of the mobile x-ray imaging system 100 may be pre-programmed such that the user does not directly control any movement, but instead initiates the start of the pre-programmed motion. The motion may comprise complex motions, with continuous motion of the isocenter.

The controller 150 is further communicatively coupled to a display device 165 for displaying one or more x-ray images acquired via the x-ray detector 107. Further, in some examples, one or more of the controller 150, the user interface 160, and the display device 165 may be positioned away from (e.g., remotely from) the remaining components of the mobile x-ray imaging system 100.

The mobile x-ray imaging system 100 may further include a torque balancing system 180 for balancing the mobile x-ray imaging system 100 when the position of one or more components of the mobile x-ray imaging system 100 is adjusted. In one example, the torque balancing system 180 comprises a plurality of motors 182, wherein the motors 182 are configured to generate balancing torques applied to the robotic arm 120. More specifically, the motors 182 generate balancing torques to balance torques generated between the C-arm gantry 110, the robotic arm 120, and the mobile base 140. To that end, the motors 182 may comprise the motors 124 of the robotic arm 120.

Non-active solutions to torque balancing, such as counterweights 186, springs (including gas-based springs), cables, and pulleys may be preferable to motor-based torque balancing. In one example, the torque balancing system 180 comprises a plurality of springs 184, wherein the springs 184 are configured to generate balancing torques applied to the robotic arm 120. More specifically, the springs 184 generate balancing torques to balance torques generated between the C-arm gantry 110, the robotic arm 120, and the mobile base 140. An example torque balancing system 180 comprising springs 184 is described further herein with regard to FIG. 8.

The mobile x-ray imaging system 100 may further include a cooling system 190 for cooling the x-ray source 105 and/or the x-ray detector 107. The cooling system 190 may comprise one or more flexible tubes and a pump, as an illustrative and non-limiting example, for providing cooling fluid to the x-ray source 105 to transfer thermal energy away from the x-ray source 105. The cooling system 190 may actively cool the x-ray source 105 and the x-ray detector 107 independently, or in some examples may cool the x-ray detector 107 by any suitable type of derivation of the cooling circuit for the x-ray source 105.

FIG. 2 shows a schematic illustration of an example mobile x-ray imaging system 200. The mobile x-ray imaging system 200 includes the components depicted in FIG. 1. For example, the mobile x-ray imaging system 200 includes an x-ray source 205 and an x-ray detector 207 mounted on a C-arm gantry 210. The C-arm gantry 210 is coupled to a mobile base 240 of the mobile x-ray imaging system 200 via a C-arm carrier 212 and a robotic arm 220. As described further herein, the C-arm carrier 212 and the robotic arm 220 may be controlled to adjust a position of an imaging isocenter 209, also referred to herein simply as isocenter 209, relative to the mobile base 240, to adjust a position of the C-arm gantry 210 relative to the mobile base 240, and/or to adjust a position of the x-ray source 205 and the x-ray detector 207 relative to the isocenter 209.

To be specific, the isocenter 209 of the C-arm gantry 210 comprises the intersection of the optical axis (defined by the focus 305 of the x-ray source 205 and the center of the x-ray detector 207 or the normal to the x-ray detector 207 that goes through the focus 305) and the C-arm rotation axis along the carrier 212. In some examples, the first link 221 is rotated at the second joint 225 relative to the second link 224 such that the first link 221 is always aligned to the isocenter. However, it should be appreciated that in other examples, the first link 221 may not be aligned with the isocenter.

The C-arm carrier 212 comprises a carrier base 213 coupled to the C-arm gantry 210 and configured to rotate the C-arm gantry 210 along a gantry track 211 in the depicted x-y plane. To that end, the carrier base 213 may include one or more motors (not shown), such as the C-arm motor 112, for sliding the C-arm gantry 210 along the gantry track 211. The C-arm gantry 210 may be rotated in the x-y plane about a rotation axis or the isocenter 209 relative to the C-arm carrier 212, such that the x-ray source 205 and the x-ray detector 207 are rotated relative to the isocenter 209 in the x-y plane.

In addition, the C-arm carrier 212 further comprises a support base 214 mechanically coupled to the carrier base 213 as depicted. The support base 214 is in turn mechanically coupled to a first link 221 of the robotic arm 220, thereby forming a first joint 222 between the first link 221 and the C-arm carrier 212. A motor 124 of the robotic arm 220 is configured to rotate the C-arm carrier 212, and thus the C-arm gantry 210, relative to the first link 221 of the robotic arm 220 at the motorized first joint 222, such that the C-arm gantry 210 rotates in the depicted y-z plane. That is, the C-arm carrier 212 rotates at the first joint 222 relative to the first link 221 in the y-z plane. In this way, the carrier base 213 and the C-arm gantry 210 coupled thereto (as well as the components mounted to the C-arm gantry 210) may rotate in the y-z plane relative to the first link 221 of the robotic arm 220. Thus, the C-arm gantry 210 and the components mounted thereon may be rotated via the C-arm carrier 212 and the first joint 222 about the isocenter 209 in three-dimensional space (e.g., in the x-y plane via the C-arm carrier 212, and in the y-z plane via the first joint 222).

Further, the first link 221 of the robotic arm 220 is mechanically coupled to a second link 224 of the robotic arm 220 at a second joint 225. The robotic arm 220 includes a motor 124 (not pictured in FIG. 2) at the joint 225 for rotating the first link 221 relative to the second link 224. In particular, the first link 221 may be rotated about the second joint 225 in the depicted x-y plane, with the motion range 226. It should be appreciated that the motion range 226 is theoretical and that in practice the first link 221, and thus the C-arm gantry 210, may not be fully rotatable around the second joint 225.

The second link 224 of the robotic arm 220 is mechanically coupled to a third link 228 of the robotic arm 220 via a third joint 227. The robotic arm 220 includes a motor 124 (not pictured in FIG. 2) at the third joint 227 for rotating the second link 224 in the x-y plane relative to the third link 228, with the motion range 229. As with the motion range 226 of the first link 221, it should be appreciated that the motion range 229 of the second link 224 relative to the third link 228 is theoretical, and that in practice the motion range of the second link 224 may only comprise a subset of the depicted motion range 229.

Further, the third link 228 of the robotic arm 220 is mechanically coupled to the mobile base 240 at a fourth joint 230. The robotic arm 220 includes a motor 124 (not pictured in FIG. 2) at the fourth joint 230 for rotating the third link 228 in the x-y plane relative to the mobile base 240, with the motion range 231. As with the motion ranges 226 and 229, the motion range 231 of the third link 228 relative to the mobile base 240 is theoretical.

Thus, the robotic arm 220 of the mobile x-ray imaging system 200 comprises a first link 221, a second link 224, and a third link 228, as well as a first joint 222, a second joint 225, a third joint 227, and a fourth joint 230. The first joint 222 provides a degree of freedom in the depicted y-z plane, while the second joint 225, the third joint 227, and the fourth joint 230 each provide a degree of freedom in the depicted x-y plane. Each joint is motorized to enable relative motion of the links of the robotic arm 220 relative to each other, as well as to the C-arm gantry 210 and the mobile base 240. By controlling the relative positions of each link, the position of the C-arm gantry 210 as well as the x-ray source 205 and the x-ray detector 207 mounted thereon are adjustable relative to the mobile base 240 in three-dimensional space.

The mobile x-ray imaging system 200 further includes a detector arm system 270 comprising one or more robotic arms configured to adjust a position of the x-ray detector 207. The detector arm system 270 may be controlled to increase or decrease the distance of the x-ray detector 207 from the C-arm gantry 210, thereby adjusting the position of the imaging center 218 of the mobile x-ray imaging system 200, which is located in the central point between the x-ray detector 207 and the x-ray source 205. As discussed further herein, the components of the mobile x-ray imaging system 200 other than the detector arm system 270 may be controlled to adjust the position of the imaging center 218 in three-dimensional space. For example, controlling the robotic arm 220 enables a translation of the imaging center 218 in the depicted x-y plane. Furthermore, rotation of the C-arm gantry 210 at the first joint 222 in the y-z plane, as well as rotation of the C-arm gantry 210 relative to the C-arm carrier 212, adjusts the relative position of the x-ray source 205 and the x-ray detector 207 relative to the imaging center 218 in three-dimensional space.

The mobile base 240 includes a plurality of wheels including driven wheels 244 and free wheels 246. The driven wheels 244 may be driven by one or more motors 242 for moving the mobile base 240 and thus the entire mobile x-ray imaging system 200. In addition to moving the mobile x-ray imaging system 200 along the x-axis (i.e., to the left and right), the motor 242 may drive the driven wheels 244 in the z direction, thus enabling the mobile x-ray imaging system 200 to be re-positioned in any orientation in the x-z plane. As an example, two motors 242 for each of the driven wheels 244 may be provided, wherein one motor 242 comprises a traction motor and a second motor 242 comprises a direction motor. In other examples, dual wheels (with differential traction motors), omnidirectional wheels, or other types of motorized wheels may be used. The free wheels 246 may not be driven by a motor. Further, as depicted, the driven wheels 244 may be positioned in the front of the mobile base 240 (i.e., on the side of the mobile base 240 closer to the C-arm gantry 210) and thus may be advantageously positioned closer to the center of gravity of the mobile x-ray imaging system 200. As discussed further herein with regard to FIGS. 14-17, in some examples the free wheels 246 may be positioned at the front side of the mobile base 240 on a structure extending towards the C-arm gantry 210. In some examples, all wheels of the mobile x-ray imaging system 200 may be driven wheels 244.

In some examples, the mobile x-ray imaging system 200 may include a high voltage generator 274 housed within the housing 245 of the mobile base 240. Providing the high voltage generator 274 within the mobile base 240 increases the weight of the mobile base 240, thus stabilizing the mobile x-ray imaging system 200. Furthermore, providing the high voltage generator 274 within the mobile base 240 eliminates the need to house the high voltage generator 274 remotely from the mobile x-ray imaging system 200, thereby eliminating long high-voltage cables typically connected to the x-ray source 205 via the tether 288 for providing the x-ray source 205 with high voltages.

The mobile x-ray imaging system 200 may further include a torque balancing system 272 for actively or passively balancing static torques generated by different articulated configurations of the robotic arms and C-arm gantry. Although the torque balancing system 272 is depicted as positioned within the mobile base 240, it should be appreciated that the torque balancing system 272 may be integrated into the robotic arm assembly and thus may be external and/or internal to the robotic arm 220. As depicted, the links of the robotic arm 220 and 230 comprise short links, and so in the depicted example the joint 230 between the third link 228 and the mobile base 240 is positioned vertically (e.g., in they direction) relatively close to the isocenter 209. In such an example, the torque balancing system 272 may comprise one or more motors, such as the motors 124 of the robotic arm 220, for generating balancing torques.

In other examples, the links of the robotic arm 220 comprise long links to provide an extended reach of the robotic arm and thus the C-arm gantry 210. In such examples, the joint 230 between the third link 228 and the mobile base 240 may be positioned vertically lower (e.g., closer to the floor). The torque balancing system 272 may comprise, in such examples, one or more springs, such as the springs 184, for generating torques to balance the mobile x-ray imaging system 200. An example configuration of a mobile x-ray imaging system with long or short links and a spring-based torque balancing system 272 is described further herein with regard to FIG. 8.

Further, a tether 288 may couple the mobile x-ray imaging system 200 to a ceiling of the room wherein the mobile x-ray imaging system 200 is installed. Power, data, and cooling may be provided via the tether 288.

In some examples, the C-arm gantry 210 may comprise a composite material to reduce the overall weight of the C-arm gantry 210 as well as providing protection of components of the C-arm gantry 210. For example, the C-arm gantry 210 may comprise a strong but lightweight composite material such that the center of gravity of the C-arm assembly, including the C-arm gantry 210 as well as the x-ray source 205 and x-ray detector 207 mounted thereon, is closer to the rotational axis or the isocenter 209. In contrast, previous approaches to constructing a C-arm gantry 210 with a heavier material would cause the center of gravity of the C-arm assembly to be away from the center of rotation or rotational axis, which coincides with the isocenter 209, and towards the C-arm gantry 210 wherein the carrier 212 is coupled as depicted in FIG. 2. Reducing the weight of the C-arm gantry 210 and thus causing the center of gravity of the C-arm assembly to be more closely aligned with the rotational axis 209 advantageously effects the control of the positioning of the C-arm gantry. The composite structure (made of a single part or a limited set of molded elements) may include additional functions such as support for detector motion, covering the tube bottom, providing conduits for cables and cooling fluid pipes, providing thermal and electrical barriers, and so on. This is in substantial contrast with typical metal C-arm structures, typically formed of curved extruded aluminum beam.

Further, in some examples, an on-board generator, a heat exchanger, and a battery may be provided at the mobile base 240 to eliminate the tether 228 and thus enable fully autonomous operation of the mobile x-ray imaging system 200.

The robotic arm 220 and the C-arm carrier 212 of the mobile x-ray imaging system 200 are depicted in a first articulated configuration. FIG. 3 shows a simplified diagram of the mobile x-ray imaging system 200 in a different articulated configuration 300, wherein the robotic arm 220 is in the first articulated configuration depicted in FIG. 2 while the detector arm system 270 is extended such that the detector 207 is closer to isocenter 209. It should be appreciated that the configuration of the mobile x-ray imaging system 200 enables an extended total range of motion for the mobile x-ray imaging system 200 relative to previous approaches.

Figure 4:
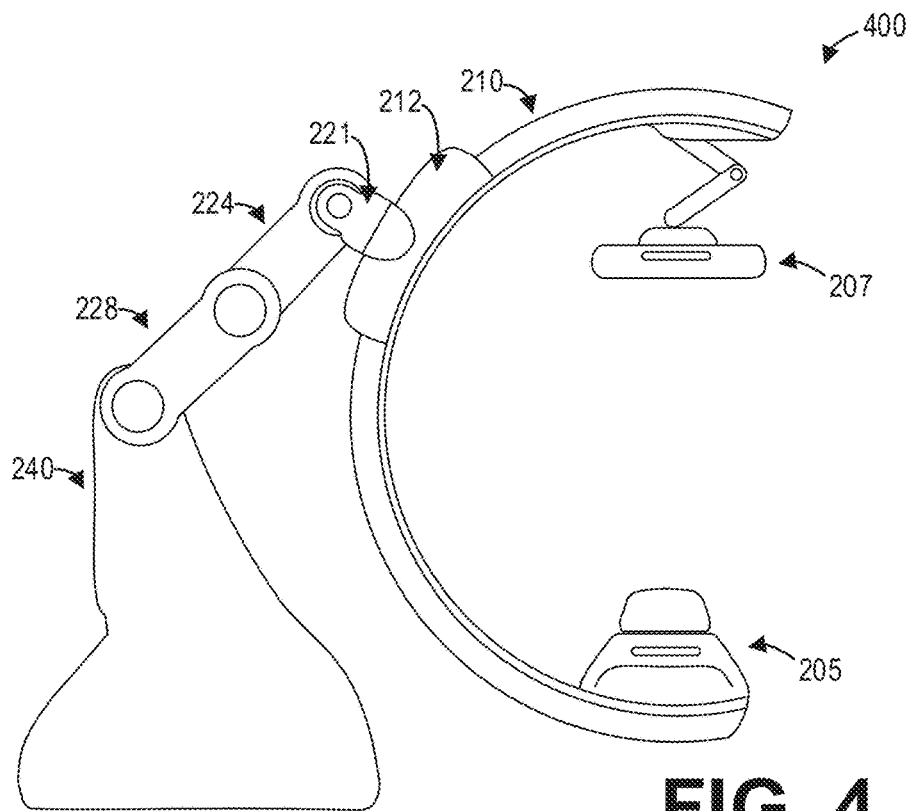
FIG. 4 shows a schematic illustration of the example mobile x-ray imaging system in a second articulated configuration according to an embodiment.
Figure 5:
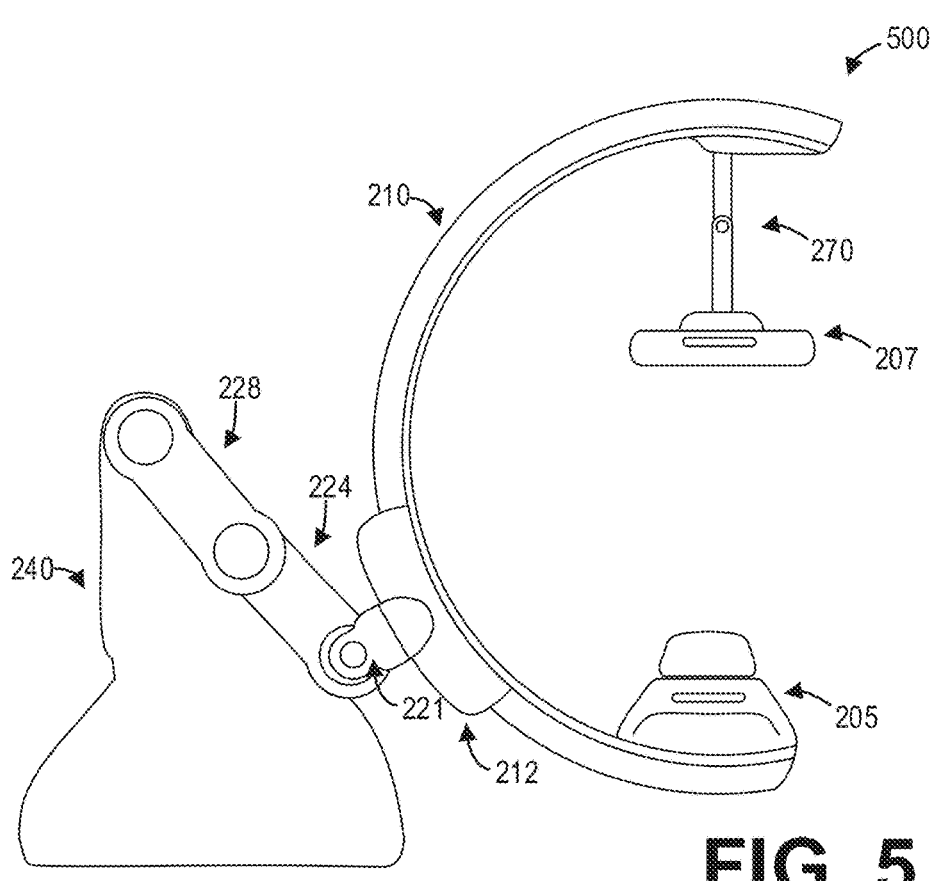
FIG. 5 shows a schematic illustration of the example mobile x-ray imaging system in a third articulated configuration according to an embodiment.

For example, FIG. 4 shows a schematic illustration of the mobile x-ray imaging system 200 in a second articulated configuration 400. FIG. 5 shows a schematic illustration of the mobile x-ray imaging system 200 in a third articulated configuration 500. Further, in the third articulated configuration 500, the x-ray detector 207 is extended away from the C-arm gantry 210 via the detector arm system 270 as depicted, thereby adjusting the position of the imaging center 218. In both examples, the C-arm gantry 210 is repositioned with respect to the C-arm carrier 212.

Figure 6:
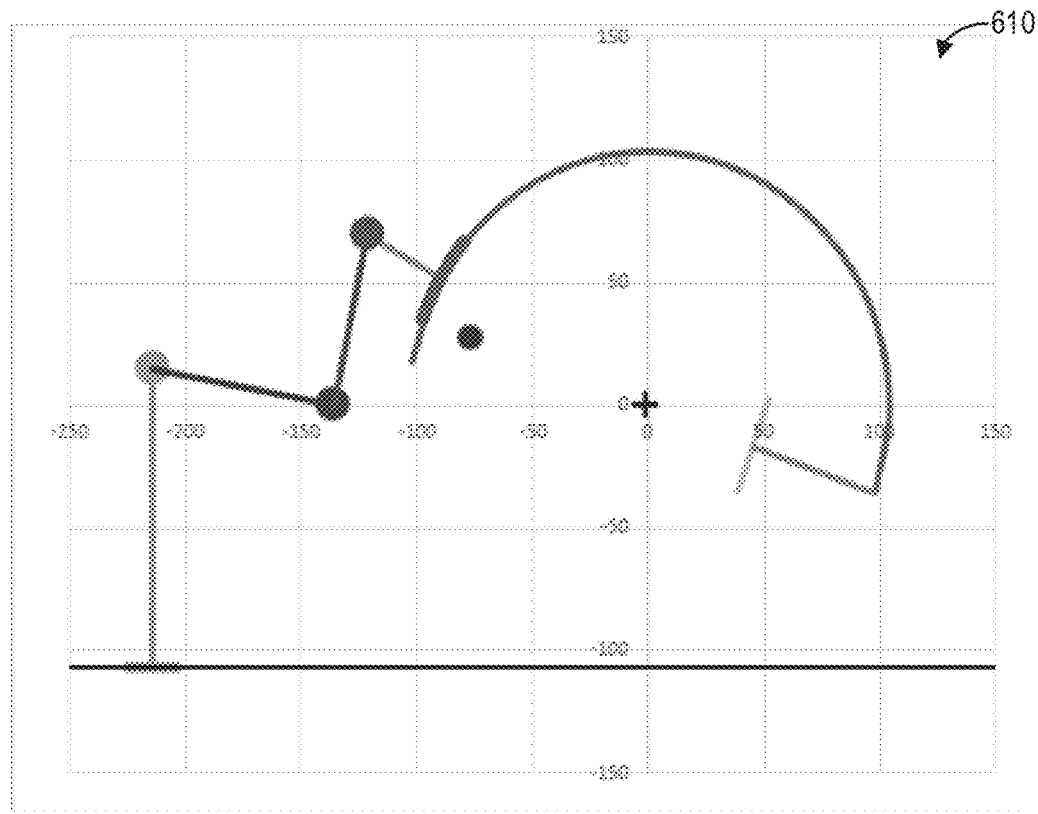
FIG. 6 shows simplified diagrams illustrating the maximum angular extension of the mobile x-ray imaging system according to an embodiment.
Figure 6:
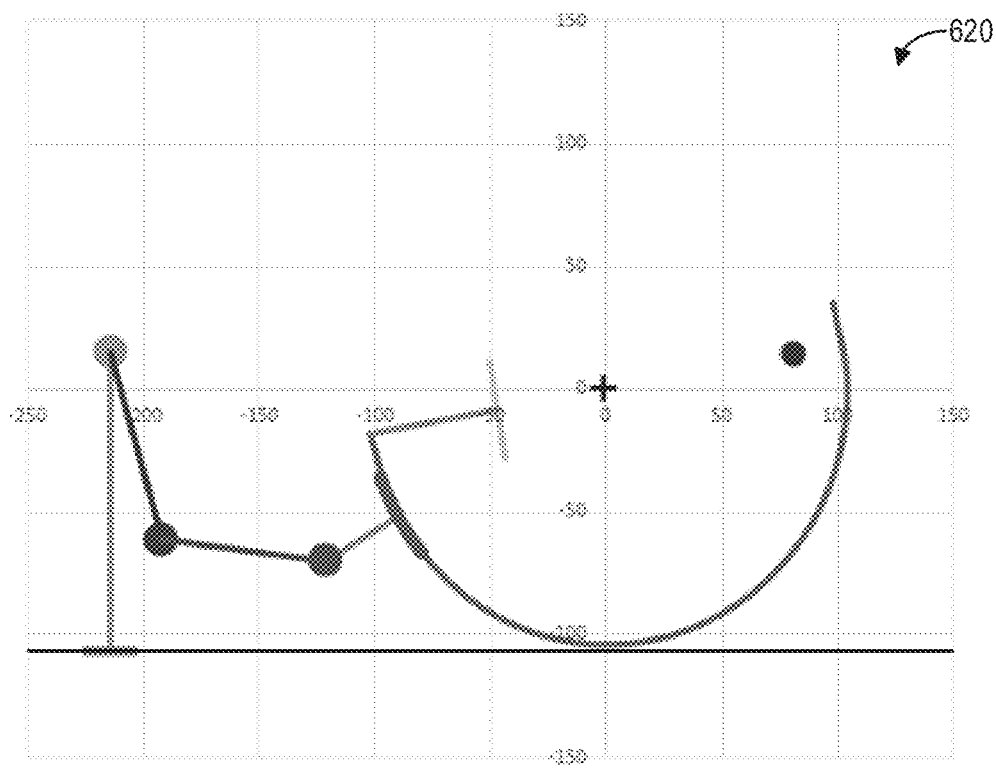

Further, FIG. 6 shows an articulated configuration 610 of the mobile x-ray imaging system 200 and another articulated configuration 620 of the mobile x-ray imaging system 200. In particular, the articulated configurations 610 and 620 depict the maximum angular extension of the C-arm gantry 210.

Figure 7:
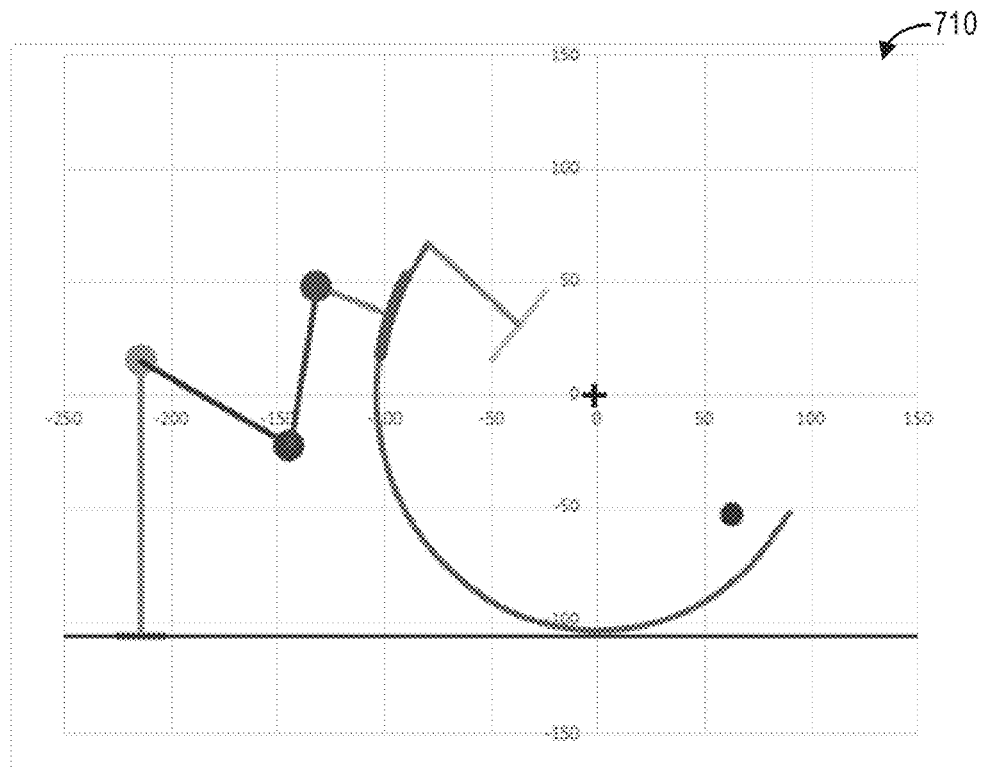
FIG. 7 shows simplified diagrams illustrating different articulated configurations for providing the same C-arm position according to an embodiment.
Figure 7:
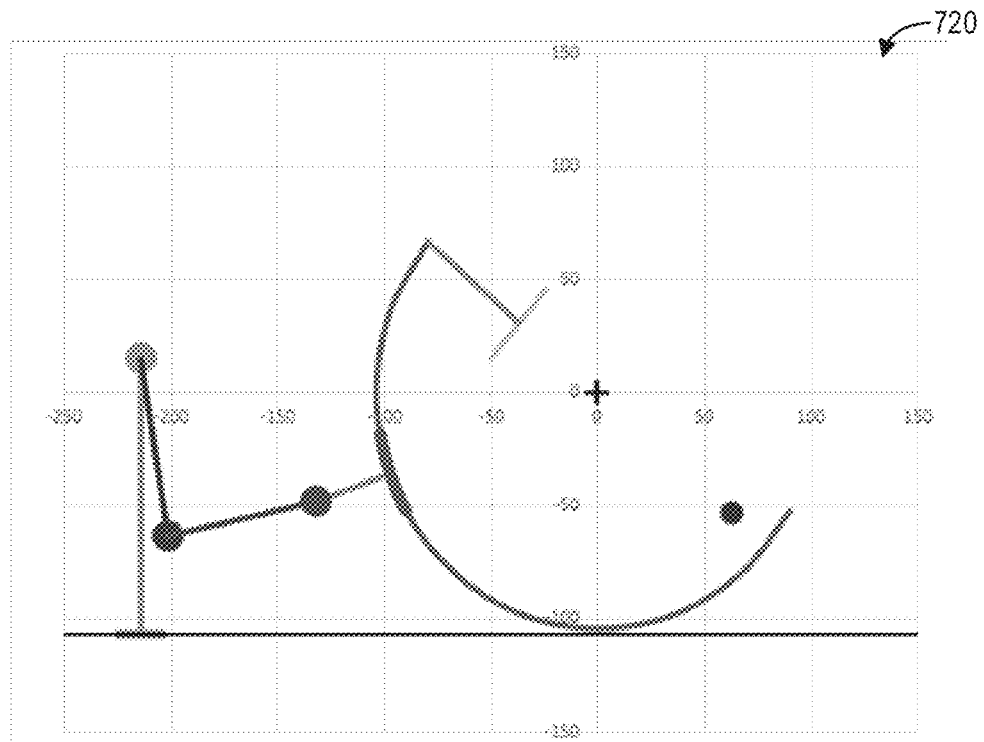
Figure 8:
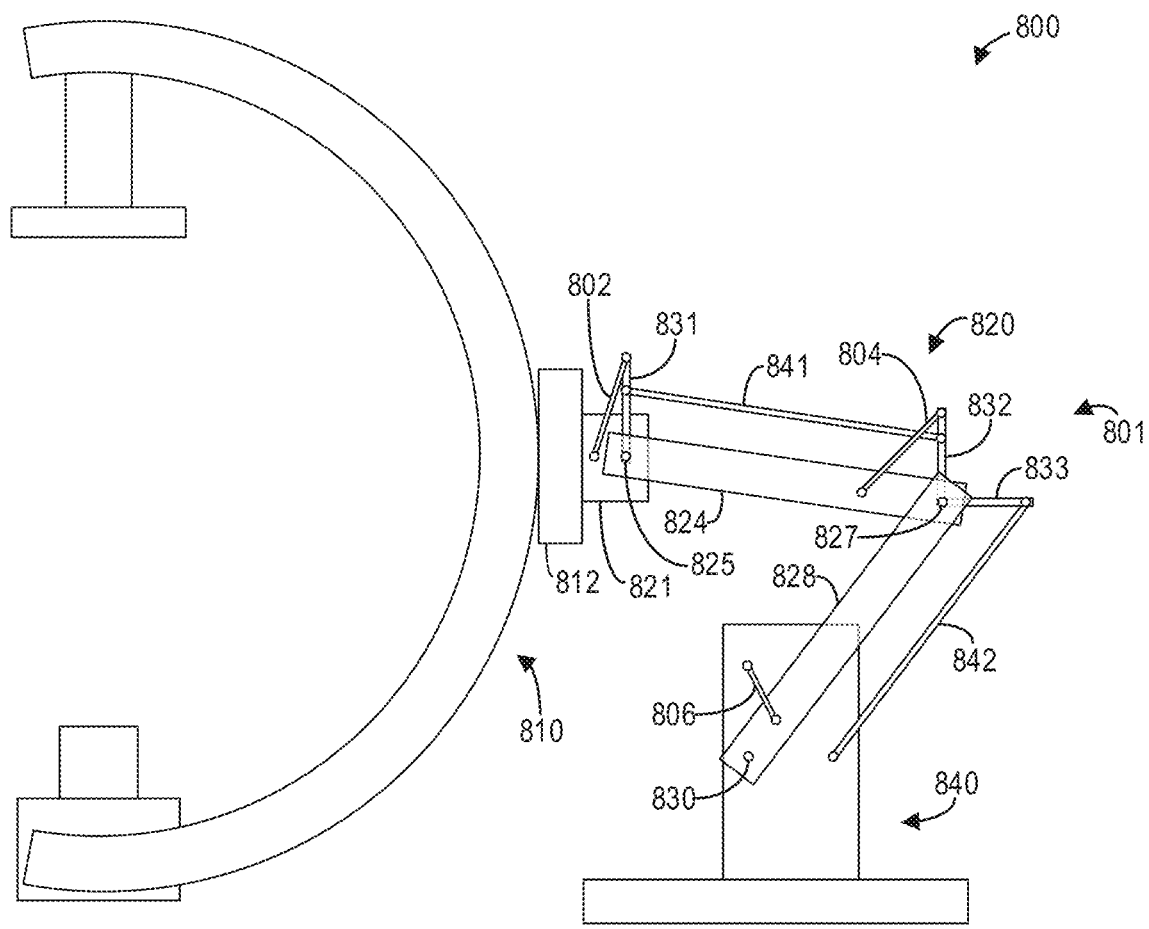
FIG. 8 shows a schematic illustration of a torque balancing system for a mobile x-ray imaging system according to an embodiment.

FIG. 7 shows the mobile x-ray imaging system 200 with the links of the robotic arm 220 in an articulated configuration 710 and another articulated configuration 720. Despite the substantially different articulated configurations 710 and 720 for the robotic arm 220, the C-arm gantry 210 is maintained in a same position relative to the isocenter 209. Thus, there are a plurality of articulated configurations for a given C-arm position.

FIG. 8 shows a schematic illustration of a torque balancing system 801 for a mobile x-ray imaging system 800. The torque balancing system 801 includes a plurality of springs for each joint of the robotic arm 820, and thus includes a first spring 802, a second spring 804, and a third spring 806. Note that the torque balancing system 801 does not include a spring for the first joint between the first link 821 of the robotic arm and the C-arm carrier 812, though in some examples the torque balancing system 801 may also include a fourth spring for the first joint between the first link 821 and the C-arm carrier 812.

The torque balancing system 801 further includes a plurality of bars extending from joints of the arm assembly, including a first bar 831 extending from the second joint 825 between the first link 821 and the second link 824, a second bar 832 extending from the third joint 827 between the second link 824 and the third link 828, and a third bar 833 extending from the second joint 827. The first bar 831 is coupled to the second bar 832 via a first mechanical link 841, while the third bar 833 is coupled to the mobile base 840 via a second mechanical link 842.

As depicted, the first spring 802 couples the first link 821 to the first bar 831 to provide a first balancing torque, the second spring 804 couples the second link 824 to the second bar 832 to provide a second balancing torque, and the third spring 806 couples the third link 828 to the mobile base 840 to provide a third balancing torque.

The configuration of the torque balancing system 801, in particular the configuration of the bars and mechanical links as depicted, enables the plurality of springs to counteract torques applied to the robotic arms and the mobile base according to the articulated configuration of the robotic arms and the C-arm gantry.

Furthermore, the third link 828 is coupled to the mobile base 840 via a fourth joint 830, such that the third link 828 may rotate about the third joint 830 relative to the mobile base 840. As discussed hereinabove, the second link 824 and the third link 828 are long links in comparison to the links of the robotic arm 220 depicted in FIG. 2. In such an example, the fourth joint 830 may be positioned closer to the floor such that the fourth joint 830 is vertically lower than isocenter of the C-arm gantry 810.

Figure 9:
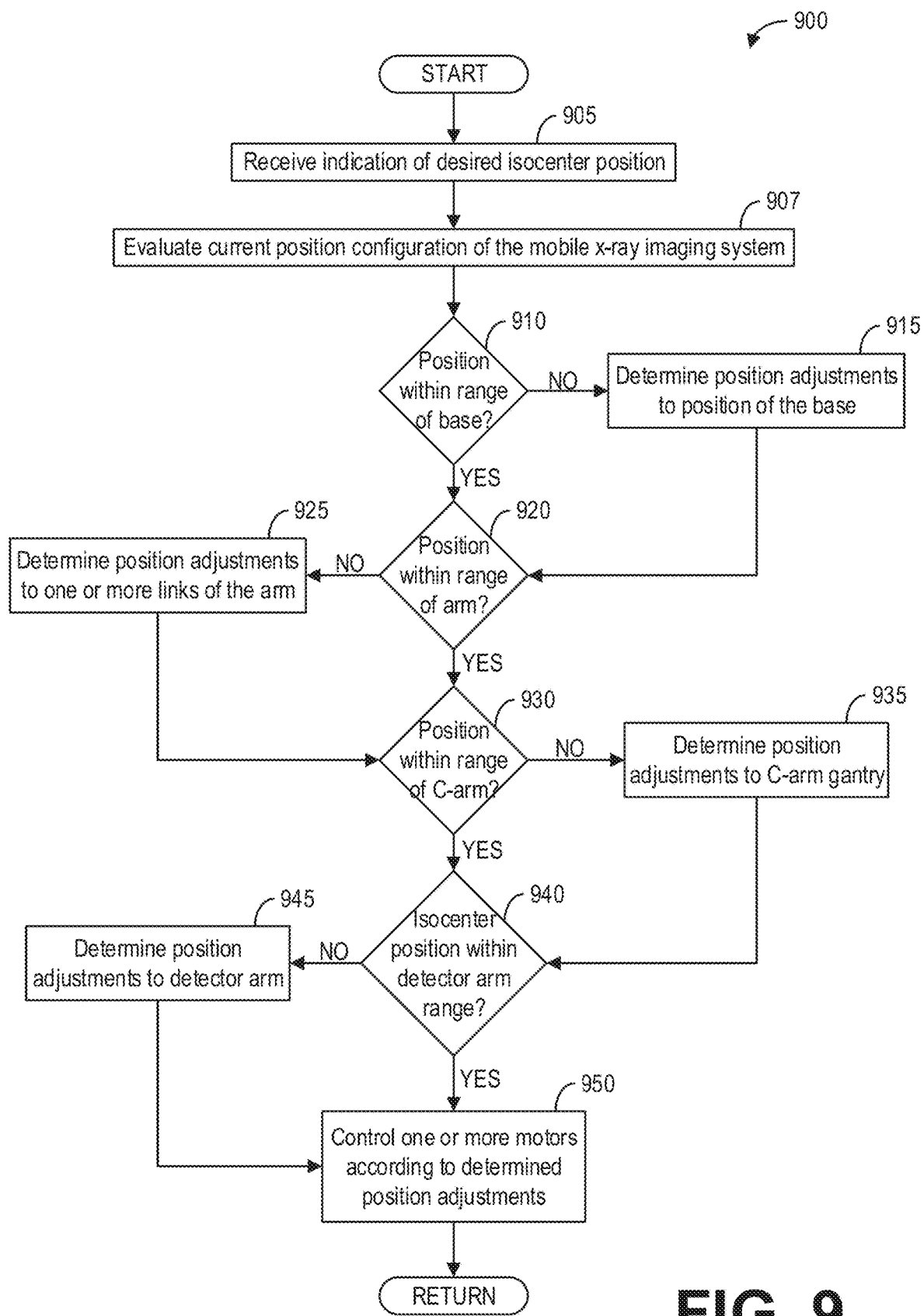
FIG. 9 shows a high-level flow chart illustrating an example method for adjusting a position of a mobile x-ray imaging system according to an embodiment.

FIG. 9 shows a high-level flow chart illustrating an example method 900 for adjusting a position of a mobile x-ray imaging system. In particular, method 900 relates to controlling one or more components of a mobile x-ray imaging system, such as mobile x-ray imaging system 200 described hereinabove, to adjust a position of an isocenter of the mobile x-ray imaging system. Method 900 is described with regard to the systems and components of FIGS. 1-8, though it should be appreciated that the method may be implemented with other systems and components without departing from the scope of the present disclosure. Method 900 may be stored as executable instructions 155 in non-transitory memory 154 of a controller 150 of the mobile x-ray imaging system 100, for example, and may be executed by a processor 152 of the controller 150.

Method 900 begins at 905. At 905, method 900 receives an indication of a desired isocenter position. The indication of the desired isocenter position may be received, for example, via a user interface such as user interface 160. The desired isocenter position may comprise an indication of a position in three-dimensional coordinates (e.g., x, y, z) and in some examples may further include an orientation of the x-ray source and detector with respect to the isocenter. As another example, the desired isocenter position may comprise a direction in which the user would like the isocenter to adjust to.

At 907, method 900 evaluates the current position configuration of the mobile x-ray imaging system. For example, method 900 evaluates the position configuration of each component of the mobile x-ray imaging system with respect to each other component, as well as the position configuration of the components of the mobile x-ray imaging system relative to the environment (e.g., the room) wherein the mobile x-ray imaging system is located. Method 900 evaluates the current position configuration of the mobile x-ray imaging system to determine position adjustments to one or more components of the mobile x-ray imaging system that will align the isocenter of the mobile x-ray imaging system with the desired isocenter position received at 905. In one example, method 900 determines a vector between the current isocenter of the mobile x-ray imaging system and the desired isocenter position. As discussed further herein, method 900 then determines position adjustments to one or more components of the mobile x-ray imaging system to move the isocenter along the vector to the desired isocenter position.

Thus, continuing at 910, method 900 determines if the desired isocenter position is within range of the mobile base. The desired isocenter position is within range of the mobile base if the desired isocenter position is achievable without adjusting the position of the mobile base. That is, the desired isocenter position is within range of the mobile base if the isocenter of the mobile x-ray imaging system may be aligned with the desired isocenter position without driving the wheels of the mobile base to translate and/or rotate the mobile base.

If the desired isocenter position is not within range of the mobile base ("NO"), method 900 continues to 915, wherein method 900 determines position adjustments to the position of the mobile base. The position adjustments may comprise rotations and/or translations of the position of the mobile base relative to a current position of the mobile base.

After determining position adjustments to the position of the mobile base at 915, or if the desired isocenter position is within range of the mobile base ("YES") at 910, method 900 continues to 920. At 920, method 900 determines if the desired isocenter position is within range of the robotic arm. The desired isocenter position is within range of the robotic arm if the isocenter may be aligned with the desired isocenter position by adjusting the position of one or more links of the robotic arm. The range of the robotic arm may be considered according to position adjustments to the mobile base determined at 915. If the desired isocenter position is not within range of the robotic arm ("NO"), method 900 continues to 925, wherein method 900 determines position adjustments to one or more links of the arm.

After determining position adjustments to one or more links of the robotic arm at 925, or if the desired isocenter position is within range of the mobile base at 920 ("YES"), method 900 continues to 930. At 930, method 900 determines if the desired isocenter position is within range of the C-arm gantry orientation. The desired isocenter position is within range of the C-arm gantry orientation if the isocenter of the mobile x-ray imaging system may be aligned with the desired isocenter position by rotating the C-arm gantry relative to the C-arm carrier and/or sliding the C-arm gantry along the track relative to the C-arm carrier as discussed hereinabove. If the desired isocenter position is not within range of the C-arm gantry orientation ("NO"), method 900 continues to 935, wherein method 900 determines position adjustments to the C-arm gantry orientation.

After determining position adjustments to the C-arm gantry orientation at 935, or if the desired isocenter position is within range of the C-arm gantry orientation at 930 ("YES"), method 900 continues to 940, wherein method 900 determines if the desired isocenter position is within range of the detector arm or detector lift. If the desired isocenter position is not within range of the detector lift ("NO"), method 900 continues to 945. At 945, method 900 determines position adjustments to the detector lift.

After determining position adjustments to the detector lift at 945, or if the desired isocenter is within range of the detector lift at 940 ("YES"), method 900 continues to 950. At 950, method 900 controls one or more motors of the mobile x-ray imaging system according to the determined position adjustments. For example, method 900 may control one or more motors to drive the wheels of the mobile base to reposition the base, control one or more motors of the robotic arm to provide a different articulated configuration of the links, control the carrier to adjust the orientation of the C-arm with respect to the carrier, and/or control the detector arm system to adjust the position of the x-ray detector. Method 900 may simultaneously control the one or more motors such that the determined position adjustments are applied simultaneously. For example, method 900 may simultaneously adjust the position of the mobile base, one or more links of the robotic arm, the gantry, and the detector arm such that the isocenter is aligned with the desired isocenter position.

It should be appreciated that the set of position adjustments to the components of the mobile x-ray imaging system may be determined such that the isocenter of the mobile x-ray imaging system is aligned with the desired isocenter position while maintaining an overall balance of the mobile x-ray imaging system. As an illustrative example, the isocenter of the mobile x-ray imaging system may be aligned with the desired isocenter position by adjusting the position of the second link of the robotic arm relative to the third link. However, if the method 900 only controls the second link to adjust the isocenter position to the desired isocenter position, the mobile x-ray imaging system will go off balance and possibly fall over. To avoid such a scenario, method 900 may determine position adjustments to the links of the robotic arm and the gantry that when applied will align the isocenter with the desired isocenter position without causing the mobile x-ray imaging system to fall over. That is, as discussed hereinabove, the motion range of each component of the robotic arm depicted in FIG. 2 is theoretical. The limits of position adjustments to the links of the robotic arm may be designed and implemented such that balance is ensured with margin even in the most extreme articulated positions. Thus, method 900 may only adjust the position of each component within such determined limits.

After applying the position adjustments, the isocenter of the mobile x-ray imaging system is aligned with the desired isocenter position. Method 900 then returns.

As an illustrative example of how the components of a mobile x-ray imaging system may be controlled to align an isocenter of the mobile x-ray imaging system with a desired isocenter position, FIG. 10 depicts a first articulated configuration 1010 of the mobile x-ray imaging system 200 with a first isocenter position 1011 and a second articulated configuration 1020 of the mobile x-ray imaging system 200 with a second isocenter position 1021. Although not explicitly depicted, the second articulated configuration 1020 may include a rotation of the C-arm gantry 210 in the y-z plane via the carrier 212.

To illustrate how the mobile x-ray imaging system 200 may adjust from the first articulated configuration 1010 to the second articulated configuration 1020, FIGS. 11-13 depict different trajectories for the different components between the two configurations. In particular, FIG. 11 includes a set of graphs 1100 illustrating basic linear trajectories of each component from the first articulated configuration 1010 to the second articulated configuration 1020, wherein each component (i.e., the second link 224, the third link 228, and the carrier 212) are controlled such that the increase in corresponding angles or positions are linear over time. The set of graphs 1100 includes a plot 1110 of the angle of the second link 224 over time, a plot 1120 of the angle of the third link 228 over time, a plot 1130 of the position of the carrier 212 relative to the track 211 of the gantry 210 over time, and a plot 1140 of the rotation angle of the C-arm gantry 210 relative to the carrier 212 over time. As depicted, the components of the mobile x-ray imaging system 200 are in the first articulated configuration 1010 at a time T1, and each component is linearly controlled over time until a time T2 when the components are in the second articulated configuration 1020. In such an example, the method 900 for controlling the mobile x-ray imaging system 200 may determine position adjustments comprising the linear trajectories depicted in FIG. 11.

However, in some instances the linear trajectories depicted in FIG. 11 may be disadvantageous or altogether impossible. For example, the C-arm gantry 210 may collide with the floor or another object within the room, or an intermediate configuration of the mobile x-ray imaging system 200 between times T1 and T2 may be unbalanced to the point that the mobile x-ray imaging system 200 falls over. Thus, the components of the mobile x-ray imaging system 200 may be controlled with non-linear trajectories to transition from the first articulated configuration 1010 to the second articulated configuration 1020.

As an illustrative example, FIG. 12 shows a set of graphs 1200 illustrating how components of a mobile x-ray imaging system may transition from the first articulated configuration 1010 to the second articulated configuration 1020, while FIG. 13 shows a set of graphs 1300 illustrating alternative trajectories for the components to transition from the first articulated configuration 1010 to the second articulated configuration 1020.

As shown in FIG. 12, the set of graphs 1200 includes a plot 1210 of a second link angle over time, a plot 1220 of a third link angle over time, a plot 1230 of a carrier track position over time, and a plot 1240 of a carrier rotation angle over time. Similarly, as shown in FIG. 13, the set of graphs 1300 includes a plot 1310 of a second link angle over time, a plot 1320 of a third link angle over time, a plot 1330 of a carrier track position over time, and a plot 1340 of a carrier rotation angle over time. As depicted, the components may be controlled with trajectories substantially different from the linear trajectories of FIG. 11. For example, the trajectories illustrated in plots 1210 and 1220 of the second and third links 224 and 228, respectively, depict the second link 224 rocking back and forth while the third link 228 first rotates counterclockwise prior to slowly rotating clockwise to reach the second articulated configuration 1020. The track position relative to the carrier 212 is then adjusted closer to the second articulated configuration 1020 while the third link 228 begins to rotate clockwise towards the second articulated configuration 1020, as depicted by the trajectories of plots 1220 and 1230. Similarly, FIG. 13 illustrates substantially different trajectories for each component, which may reflect a different torque balancing system of the mobile x-ray imaging system 200 or different obstacles within the room wherein the mobile x-ray imaging system 200 is positioned, for example.

Figure 14:
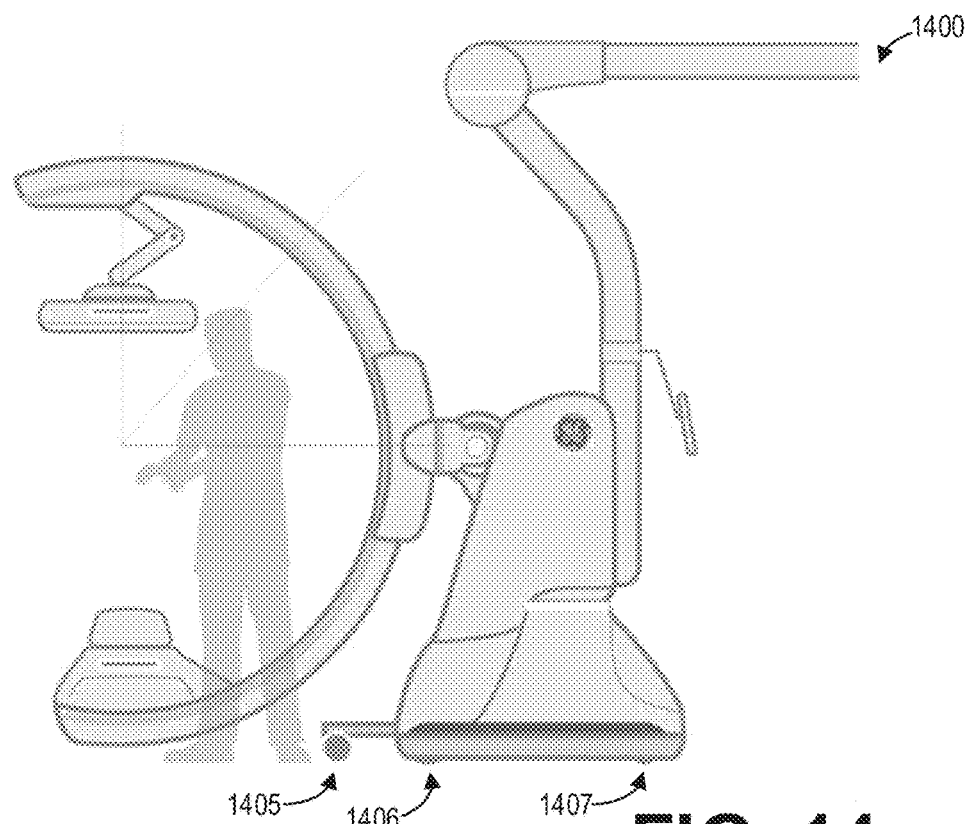
FIG. 14 shows a side pictorial view of an example mobile x-ray imaging system according to an embodiment.
Figure 15:
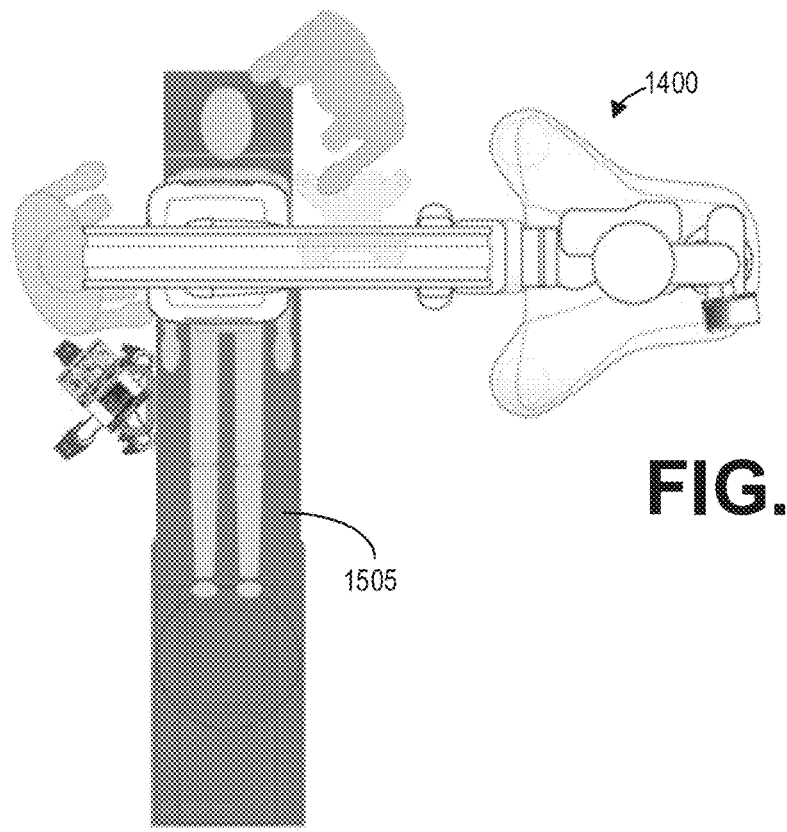
FIG. 15 shows a top pictorial view of the example mobile x-ray imaging system of FIG. 14.

FIG. 14 shows a side pictorial view of an example mobile x-ray imaging system 1400 according to an embodiment. FIG. 15 shows a top pictorial view of the example mobile x-ray imaging system 1400, while FIGS. 16 and 17 show perspective pictorial views of the example mobile x-ray imaging system 1400. As depicted in FIG. 14, the mobile x-ray imaging system 1400 includes motorized wheels 1406 positioned at a center of gravity of the mobile x-ray imaging system 1400. The mobile x-ray imaging system 1400 further includes one or more free or un-motorized wheels 1405 positioned on a structure extending from the mobile base towards the C-arm gantry, as depicted. In some examples, the mobile x-ray imaging system 1400 includes one or more free wheels 1407 positioned at a rear side of the mobile base. Furthermore, FIGS. 15-17 depict the mobile x-ray imaging system 1400 positioned relative to a table 1505, which illustrates how the C-arm gantry may be selectively controlled to adjust the position of the x-ray source and detector relative to the table 1505.

As an example of re-positioning the isocenter relative to the table 1505, FIG. 18 shows a set of simplified diagrams illustrating example articulated configurations for adjusting the isocenter position. As depicted by the configuration 1810, the isocenter may be translated away from the mobile base. As depicted by the configuration 1820, the isocenter may be translated vertically from the floor and away from the mobile base. As depicted by the configuration 1830, the isocenter may be translated towards the mobile base. As depicted by the configuration 1840, the isocenter may be translated vertically and towards the mobile base. Moving the isocenter up allows adaptation of the table height to a comfortable working position for the doctor, or the height of the anatomy in particular surgeries.

It should be appreciated that the robotic arm, aside from adjusting the isocenter of the mobile x-ray imaging system, further allows rotation of the C-arm gantry around a point other than the isocenter. As an illustrative example, FIG. 19 shows a set of simplified diagrams illustrating a dynamic rotation around a point 1911 different from the isocenter 209. In particular, the C-arm gantry 210 rotates around the point 1911, which is a limit of the x-ray beam 1905 generated at the focus 305 of the x-ray source. The isocenter trajectory is thus an arc of a circle. Specifically, the mobile x-ray imaging system shifts from the first articulated configuration 1910 to the second articulated configuration 1920 to rotate the C-arm gantry 210 around the point 1911, and then to the third articulated configuration 1930 to further rotate the C-arm gantry 210 around the point 1911, where the isocenter 209 is different from the point 1911 in each configuration. Any arbitrary trajectory is possible, within motion range of every joint, including translations, circular rotations, elliptic rotation, a combination of linear and circular segments, and so on.

Figure 20:
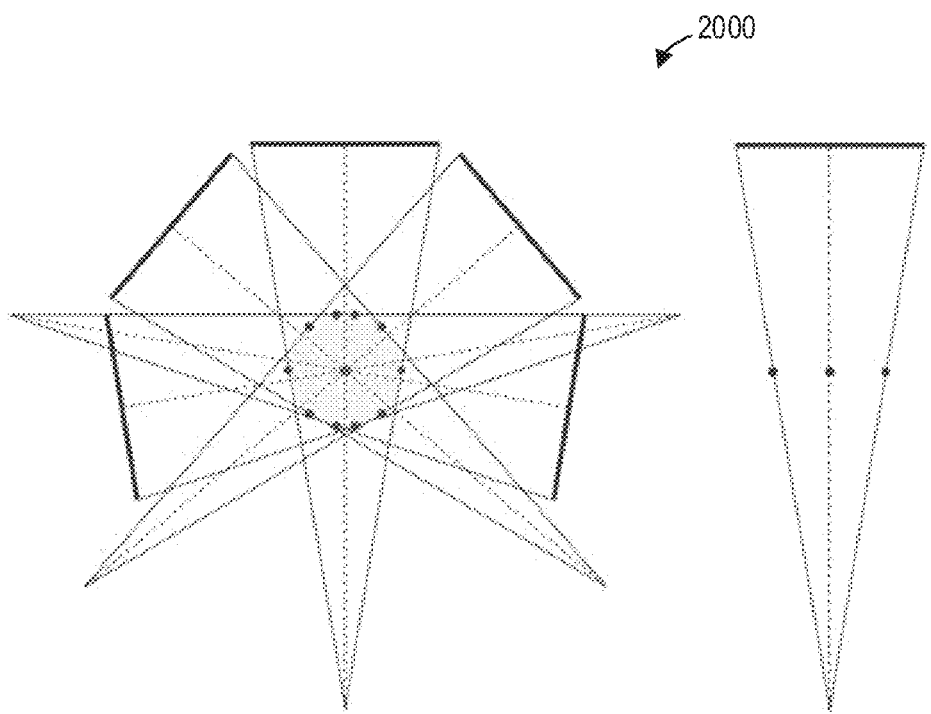
FIGS. 20-25 depict example trajectories for performing cone beam computed tomography with a mobile x-ray imaging system according to an embodiment.
Figure 21:
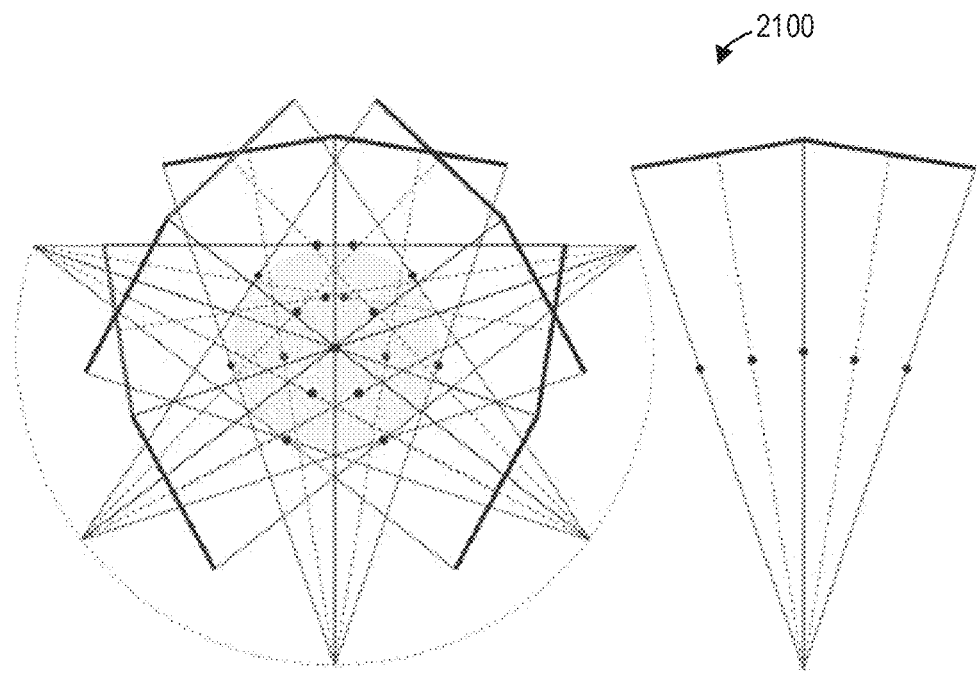
Figure 22:
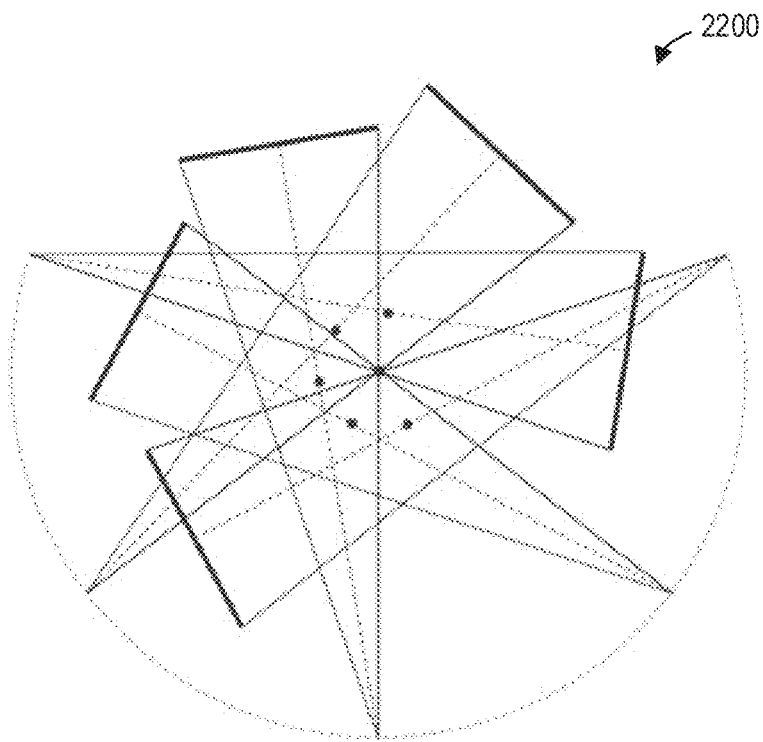
Figure 23:
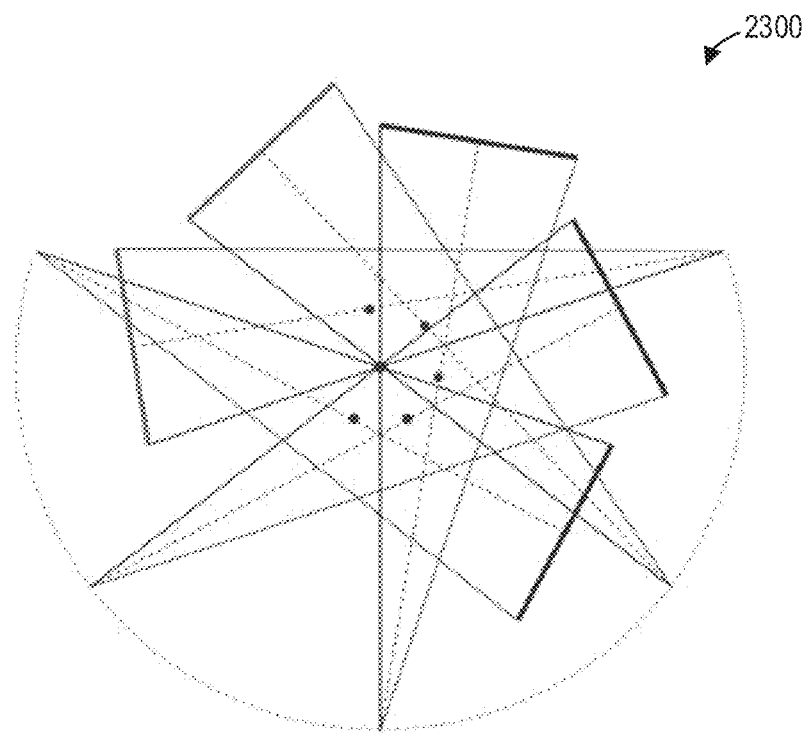

The ability to adjust the position of the C-arm gantry relative to isocenter with different trajectories allows the mobile x-ray imaging system to be used for cone beam computed tomography. As an illustrative example of why the mobile x-ray imaging system may be rotated around a point different from isocenter, FIGS. 20-25 depict example trajectories for performing cone beam computed tomography (CBCT) with a mobile x-ray imaging system according to an embodiment. In particular, FIG. 20 shows a trajectory 2000 for standard CBCT. The detector and source are rotated around the isocenter in a single rotation, depicted here as approximately 200 degrees (e.g., 180 degrees plus the cone angle). The reconstructed volume is shown in gray. By rotating the C-arm gantry about a point different from isocenter as described with regard to FIG. 19, large field of view (LFOV) CBCT is possible with dual rotations. For example, as depicted in FIG. 21, the trajectory 2100 includes a first rotation around a first center of rotation and a second rotation around a second center of rotation. Each rotation around a virtual center is approximately 220 degrees (e.g., 120 degrees plus the virtual cone angle). FIG. 22 depicts the first trajectory 2200 for the first rotation, while FIG. 23 depicts the trajectory 2300 for the second rotation. As depicted in FIG. 21, the reconstructed FOV is twice the diameter of the FOV of the standard CBCT volume depicted in FIG. 20. Thus, a twice-as-large reconstructed volume may be obtained by simulating a twice-as-large detector.

Figure 24:
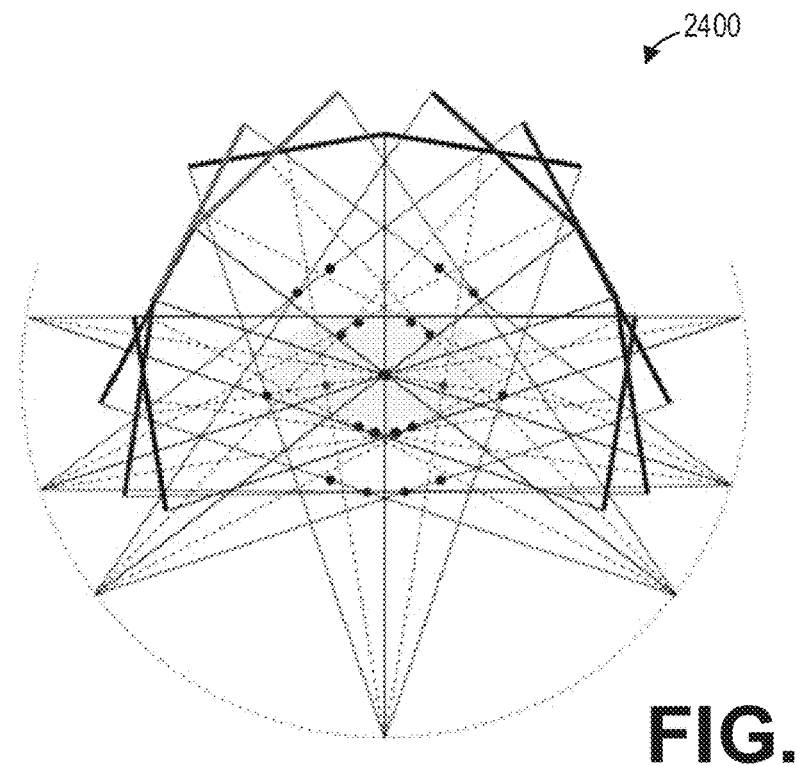
Figure 25:
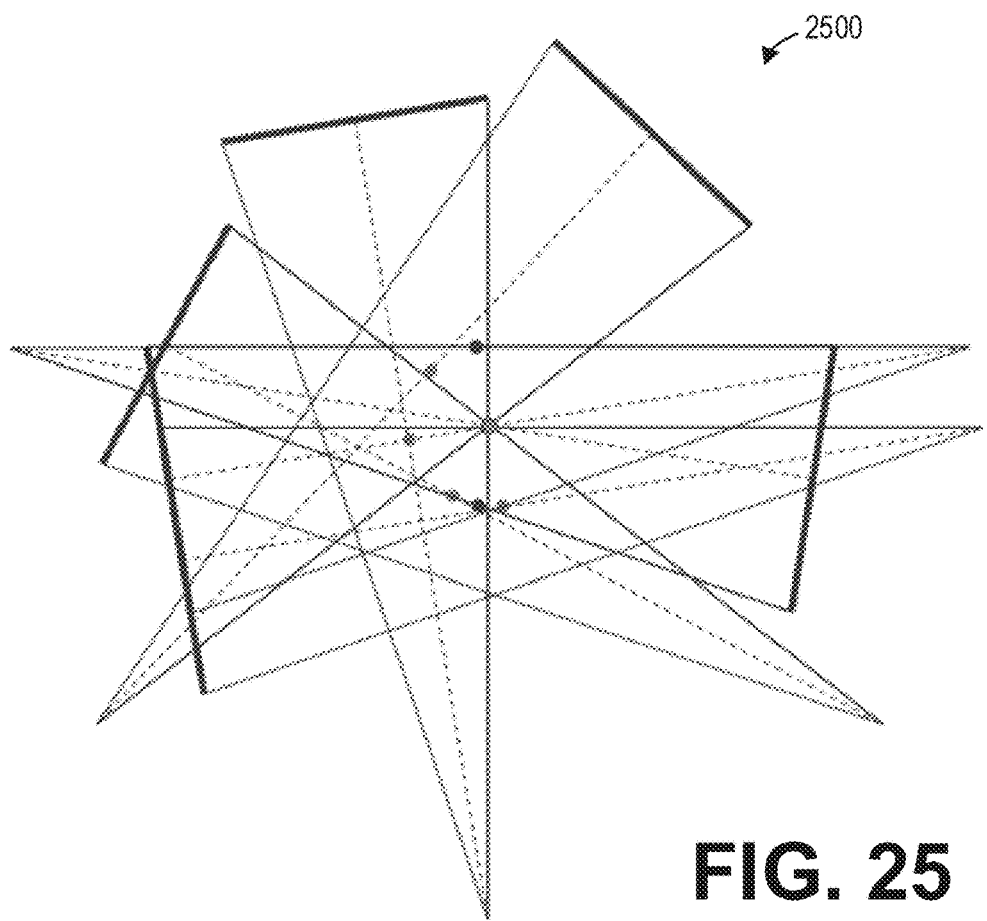

As yet another example of how the expanded isocenter trajectories enabled by the mobile x-ray imaging system described herein may be used for different imaging scenarios, FIGS. 24 and 25 depict trajectories 2400 and 2500 for a reconstructed volume with an elliptical cross-section. The trajectory of the isocenter is an arch of a circle and a translation. Such an option may be selected in cases where the rotation range of the C-arm gantry is insufficient for implementing the LFOV CBCT discussed hereinabove.

Figure 26:
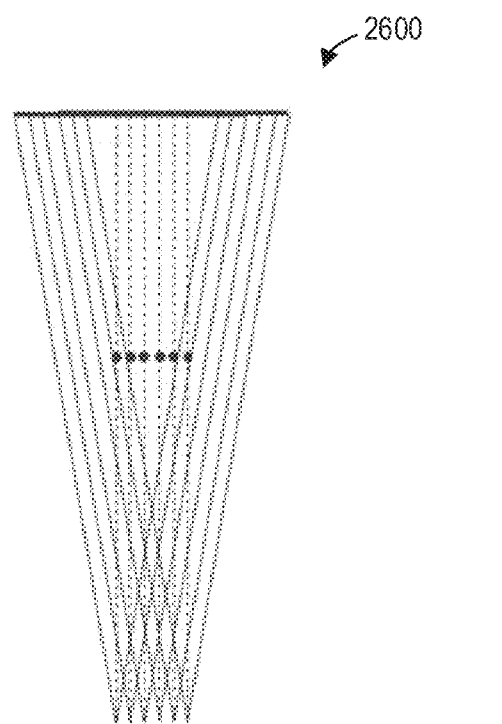
FIG. 26 depicts an example trajectory for performing linear tomosynthesis with a mobile x-ray imaging system according to an embodiment.

Finally, FIG. 26 depicts an example trajectory 2600 for performing linear tomosynthesis with a mobile x-ray imaging system. The imaging chain is simply shifted and images are acquired at regular intervals. The trajectory 2600 thus allows tomosynthetic-type reconstruction. As the C-arm gantry can be rotated in three-dimensional space, the trajectory 2600 may be performed in any orientation, thus allowing the most favorable orientation for reconstructing the object of interest. Further, stereoscopy is a variation of the same mode, comprising acquisition of a pair of images with moderate separation (e.g., five centimeters apart). A pair of images (e.g., a stereo snapshot) may be acquired, or a low frequency stereo cino mode may be used (i.e., oscillation between two positions).

FIGS. 1-8, 10, and 14-18 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

A technical effect of the disclosure includes the increased displacement of a C-arm gantry for an x-ray imaging system. Another technical effect of the disclosure includes the simultaneous control of multiple components of a mobile x-ray imaging system to adjust an isocenter of the mobile x-ray imaging system.

In on embodiment, a system comprises a gantry with an x-ray source and an x-ray detector mounted thereon opposite each other, a carrier coupled to the gantry and configured to rotate the gantry relative to the carrier, and a robotic arm coupling the carrier to a base, the robotic arm comprising at least three links and four joints.

In a first example of the system, the base comprises a mobile base, and the system further comprises a set of wheels driven by one or more motors, the set of wheels coupled to the mobile base. In a second example of the system optionally including the first example, the system further comprises a torque balancing system for countering static torques generated by a configuration of the at least three links of the robotic arm, the gantry, and the base. In a third example of the system optionally including one or more of the first and second examples, the torque balancing system comprises a plurality of springs, each spring configured to apply a balancing torque near a corresponding rotational joint of the at least three links of the robotic arm, the gantry, and the mobile base. In a fourth example of the system optionally including one or more of the first through third examples, the torque balancing system comprises a counterweight system. In a fifth example of the system optionally including one or more of the first through fourth examples, the at least three links of the robotic arm are movable in a first plane relative to the mobile base, wherein a joint of the robotic arm between a link of the robotic arm and the carrier is configured to rotate the carrier relative to the link in a plane perpendicular to the first plane, and wherein the carrier is configured to rotate the gantry relative to the carrier along a track of the gantry. In a sixth example of the system optionally including one or more of the first through fifth examples, the system further comprises a high voltage generator positioned and housed within the mobile base for providing high voltages to the x-ray source. In a seventh example of the system optionally including one or more of the first through sixth examples, the gantry is C-shaped, and the x-ray source and the x-ray detector are mounted at opposite ends of the C-shaped gantry. In an eighth example of the system optionally including one or more of the first through seventh examples, the system further comprises a controller and a user interface, wherein the controller receives a desired isocenter position via the user interface, and wherein the controller controls one or more of the at least three links of the robotic arm to adjust an isocenter of the gantry to the desired isocenter position. In a ninth example of the system optionally including one or more of the first through eighth examples, the controller simultaneously controls the one or more of the at least three links of the robotic arm to adjust the isocenter to the desired isocenter position. In a tenth example of the system optionally including one or more of the first through ninth examples, a vertical height of a coupling between the second robotic arm and the mobile base is inversely related to a length of the first and second robotic arms.

In another embodiment, a method for a mobile x-ray imaging system comprising receiving an indication of a desired isocenter position, calculating position adjustments to one or more components of the mobile x-ray imaging system, and controlling one or more motors to adjust positions of the one or more components to align an isocenter of the mobile x-ray imaging system with the desired isocenter position.

In a first example of the method, the one or more motors are controlled simultaneously to simultaneously adjust the positions of the one or more components. In a second example of the method optionally including the first example, the position adjustments are calculated according to a current isocenter position and the desired isocenter position. In a third example of the method optionally including one or more of the first and second examples, controlling the one or more motors to adjust the positions of the one or more components comprises controlling one or more motors of a mobile base, a carrier coupled to a C-shaped gantry, a first link coupled to the carrier, a second link coupled to the first link, and a third link coupling the second link to the mobile base. In a fourth example of the method optionally including one or more of the first through third examples, the method further comprises controlling the one or more motors to adjust the positions of the one or more components to dynamically rotate the one or more components around a point different from the isocenter during imaging.

In yet another embodiment, a system comprises a C-shaped gantry with an x-ray source and an x-ray detector mounted thereon, a carrier coupled to the C-shaped gantry and configured to translate the C-shaped gantry relative to the carrier, a first link of a robotic arm coupled to the carrier at a first joint, the carrier rotatable at the first joint in a first plane relative to the first link, a second link of the robotic arm coupled to the first link at a second joint, the first link rotatable at the second joint relative to the second link in a second plane perpendicular to the first plane, a third link of the robotic arm coupled to the second link at a third joint, the second link rotatable at the third joint relative to the third link in the second plane, a mobile base coupled to the third link at a fourth joint, the third link rotatable at the fourth joint relative to the mobile base in the second plane, and a controller configured with instructions in non-transitory memory that when executed causes the controller to: receive a desired isocenter position; and control one or more of the carrier, the first link, the second link, the third link, and the mobile base to adjust an isocenter of the x-ray source and the x-ray detector to the desired isocenter position.

In a first example of the system, the system further comprises a user interface communicatively coupled to the controller, wherein the controller receives the desired isocenter position via the user interface. In a second example of the system optionally including the first example, the controller is further configured to calculate position adjustments to one or more of the carrier, the first link, the second link, the third link, and the mobile base to align an the isocenter with the desired isocenter position. In a third example of the system optionally including one or more of the first and second examples, the controller simultaneously controls the one or more of the carrier, the first link, the second link, the third link, and the mobile base to adjust the isocenter.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:
    a gantry with an x-ray source and an x-ray detector mounted thereon opposite each other;
    a carrier coupled to the gantry and configured to rotate the gantry along a gantry track in a first plane relative to the carrier;
    a robotic arm coupling the carrier to a base, the robotic arm comprising at least three links and four joints, wherein a joint of the robotic arm coupling the carrier to a link of the robotic arm is configured to rotate the carrier relative to the link in a plane perpendicular to the first plane; and
    a controller configured with instructions in non-transitory memory that when executed causes the controller to:
        control the x-ray detector and the x-ray source to image a subject; and
        while controlling the x-ray detector and the x-ray source to image the subject, simultaneously control the carrier to rotate the gantry and the robotic arm to a plurality of articulated configurations according to a trajectory,
    wherein a torque balancing system configured to counter static torques generated by a configuration of the at least three links of the robotic arm, the gantry, and the base; wherein the torque balancing system comprises a plurality of springs, each spring configured to apply a balancing torque near a corresponding rotational joint of the at least three links of the robotic arm, the gantry, and the base.

2. The system of claim 1, wherein the base comprises a mobile base, and further comprising a set of wheels driven by one or more motors, the set of wheels coupled to the mobile base.

3. The system of claim 1, wherein the at least three links of the robotic arm are movable in a plane relative to the base.

4. The system of claim 1, further comprising a high voltage generator positioned and housed within the base for providing high voltages to the x-ray source.

5. The system of claim 1, wherein the gantry is C-shaped, wherein the x-ray source and the x-ray detector are mounted at opposite ends of the C-shaped gantry, and wherein the trajectory comprises a dynamic trajectory for cone beam imaging or linear tomosynthesis.

6. The system of claim 1, further comprising a user interface, wherein the controller receives a desired isocenter position via the user interface, and wherein the controller controls one or more of the at least three links of the robotic arm to adjust an isocenter of the gantry to the desired isocenter position.

7. The system of claim 1, wherein, to control the carrier and the robotic arm according to the trajectory, the controller is configured with instructions in the non-transitory memory that when executed causes the controller to:
    simultaneously control the carrier to rotate the gantry and the robotic arm to adjust a position of the carrier to dynamically rotate the gantry about a point different from an isocenter of the gantry.

8. The system of claim 6, wherein the controller simultaneously controls the carrier and the one or more of the at least three links of the robotic arm to adjust the isocenter to the desired isocenter position.

9. A system, comprising:
    a C-shaped gantry with an x-ray source and an x-ray detector mounted thereon;
    a carrier coupled to the C-shaped gantry and configured to translate the C-shaped gantry relative to the carrier along a gantry track;
    a first link of a robotic arm coupled to the carrier at a first joint, the carrier rotatable at the first joint in a first plane relative to the first link;
    a second link of the robotic arm coupled to the first link at a second joint, the first link rotatable at the second joint relative to the second link in a second plane perpendicular to the first plane;
    a third link of the robotic arm coupled to the second link at a third joint, the second link rotatable at the third joint relative to the third link in the second plane;
    a mobile base coupled to the third link at a fourth joint, the third link rotatable at the fourth joint relative to the mobile base in the second plane; and
    a controller configured with instructions in non-transitory memory that when executed causes the controller to:
        receive a desired isocenter position;
        control the carrier, the first link, the second link, the third link, and the mobile base to adjust an isocenter of the x-ray source and the x-ray detector to the desired isocenter position;
        control the x-ray source and the x-ray detector to image a subject; and
        while controlling the x-ray source and the x-ray detector to image the subject, control the carrier, the first link, the second link, the third link, and the mobile base to dynamically rotate the x-ray source and the x-ray detector around a point different from the isocenter of the system.

10. The system of claim 9, further comprising a user interface communicatively coupled to the controller, wherein the controller receives the desired isocenter position via the user interface.

11. The system of claim 9, wherein the controller is further configured to calculate position adjustments to one or more of the carrier, the first link, the second link, the third link, and the mobile base to align the isocenter of the x-ray source and the x-ray detector with the desired isocenter position.

12. The system of claim 9, wherein the controller simultaneously controls the one or more of the carrier, the first link, the second link, the third link, and the mobile base to adjust the isocenter of the x-ray source and the x-ray detector.

* * * * *